United States Patent [19]

Hiltmann et al.

[11] 4,110,472

[45] Aug. 29, 1978

[54] DERIVATIVES OF 1-(DISUBSTITUTED PHENOXY)-3-AMINO-2-HYDROXYPROPANES

[75] Inventors: Rudolf Hiltmann; Arend Heise; Stanislav Kazda; Friedrich Hoffmeister, all of Wuppertal, Fed. Rep. of Germany

[73] Assignee: Bayer Aktiengesellschaft, Fed. Rep. of Germany

[21] Appl. No.: 732,118

[22] Filed: Oct. 13, 1976

[30] Foreign Application Priority Data

Oct. 23, 1975 [DE] Fed. Rep. of Germany ....... 2547524

[51] Int. Cl.² .......................... A01N 9/24; C07C 93/06
[52] U.S. Cl. ............................... 424/330; 260/307 C; 260/307 D; 260/345.1; 260/348.49; 260/456 P; 260/459 R; 260/501.18; 260/501.19; 260/570 R; 260/570.6; 260/562 P; 260/612 R; 260/612 D; 260/348.58; 260/348.63; 424/309; 424/311; 424/316; 560/19; 560/21; 560/155
[58] Field of Search ............ 260/570.7, 501.18, 501.19

[56] References Cited

U.S. PATENT DOCUMENTS 3,758,583   9/1973   Nelson et al. .................... 260/570.7

Primary Examiner—Robert V. Hines
Attorney, Agent, or Firm—Jacobs & Jacobs

[57] ABSTRACT

N-Diphenylmethyl and o-biphenylenemethyl derivatives of 1-(disubstituted phenoxy)-3-amino-2-hydroxypropane and their salts are useful for combatting cerebrovascular insufficiency and producing psychostimulation in humans and other animals. The compounds, of which 1-(2-methoxy-4-allylphenoxy)-2-hydroxy-3-diphenylmethylamino-propane is a typical embodiment, can be prepared by a number of synthetic routes.

20 Claims, 8 Drawing Figures

COMPOUND A, DOGS, INTRAVENEOUSLY
(FENTANYL ANALGESIA)

COMPOUND A, DOGS, INTRAVENEOUSLY
(FENTANYL ANALGESIA)

BENCYCLAN, DOGS, INTRAVENEOUSLY
(FENTANYL ANALGESIA)

DERIVATIVES OF 1-(DISUBSTITUTED PHENOXY)-3-AMINO-2-HYDROXYPROPANES

DETAILED DESCRIPTION

Figure 1:
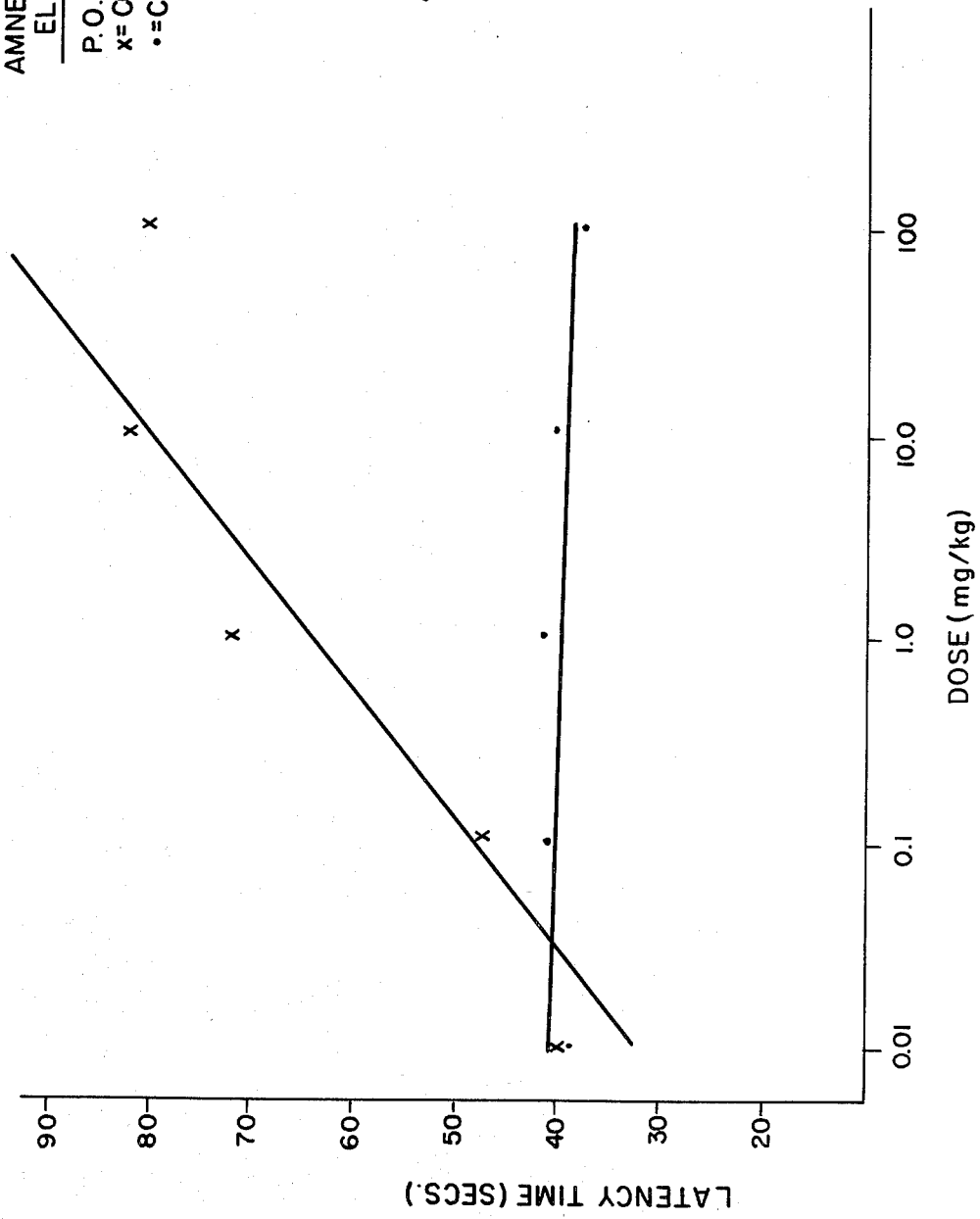

The present invention relates to new 1-(disubstituted phenoxy)-3-amino-2-hydroxypropane derivatives, to their preparation and therapeutic use in cerebrovascular disorders and to pharmaceutical compositions adapted to that use.

A number of phenol ethers of 3-amino-2-hydroxypropane, in which the amino group is substituted by alkyl, such as isopropyl or t-butyl, or by phenyl alkyl are known. Pharmacologically, compounds of this type block the adrenergic β-receptors in various organs and some are used therapeutically. (Ehrhart/Ruschig, Arzneimittel, 2nd Ed., 1971, Vol. 2, page 179 and DOS 2,021,101). Derivatives of benzhydrylamine have been available commercially as antihistamines for a relatively long time. (Ehrhart/Ruschig, 10C, Cit., Vol. 1, page 314).

The present invention pertains to 1-(disubstituted phenoxy)-3-amino-2-hydroxypropanes of the formula:

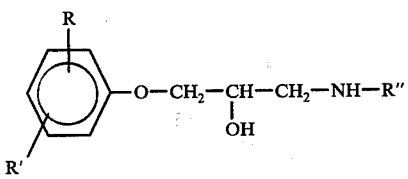

in which
each of R and R′, individually, is alkyl, alkenyl, alkoxy, carbalkoxy or chloro and
R″ is diphenylmethyl or fluorenyl.

The invention also pertains to the acid addition salts thereof, and to condensation products thereof with aldehydes, ketones and carbonic acid.

In a first embodiment, the invention pertains to compounds selected from the group consisting of (a) 1-(disubstituted phenoxy)-2-hydroxypropylamine derivatives of Formula I
wherein
R is lower alkyl, lower alkenyl, lower alkoxy, carbo(-lower alkoxy), or chloro;
R′ is lower alkyl, lower alkenyl, lower alkoxy, carbo(lower alkoxy), or chloro; and
R″ is diphenylmethyl or fluoren-9-yl;
(b) the pharmaceutically acceptable acid addition salts thereof and
(c) the cyclic condensation products thereof with carbonic acid or an aldehyde or ketone.

A further embodiment pertains to such cyclic condensation products with an aldehyde or ketone wherein the products have the formula:

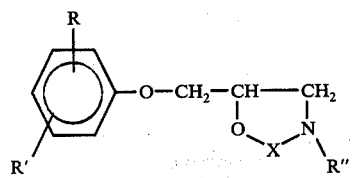

in which
R, R′ and R″ are as defined above and
X is lower alkylidene or phenyl(lower alkylidene).

A further embodiment pertains to such cyclic condensation products with carbonic acid which products have the formula:

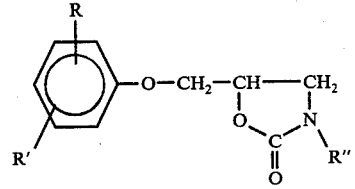

wherein
R, R′ and R″ are as defined above.

A further embodiment of the present invention pertains to compounds of the formula:

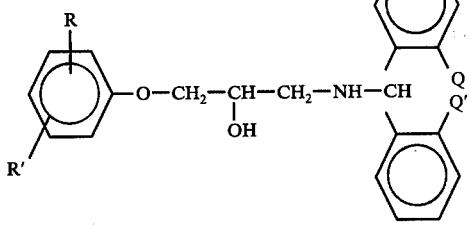

wherein each of R and R′ is selected from the group consisting of alkyl of 1 to 6 carbon atoms; alkenyl of 2 to 7 carbon atoms; alkoxy of 1 to 6 carbon atoms, carbalkoxy of 2 to 7 carbon atoms, or chloro; and
Q and Q′, when taken independently, are each hydrogen or, when taken together, are a carbon-carbon bond,
and to the pharmaceutically acceptable acid addition salts thereof.

A further embodiment pertains to compounds wherein each of R and R′, independently of the other, is alkyl of 1 to 3 carbon atoms, alkenyl of 3 carbon atoms, alkoxy of 1 to 3 carbon atoms, carbomethoxy, carbethoxy or chloro.

A further embodiment pertains to compounds wherein each of R and R′, independently of the other, is methyl, ethyl, propyl, allyl, propenyl, methoxy, ethoxy, carbomethoxy, carbethoxy or chloro.

A further embodiment pertains to compounds wherein R is 2-methoxy or 2-ethoxy and R′ is n-propyl, allyl or propenyl in 4- or 5-position.

A further embodiment pertains to compounds wherein each of R and R′ are chloro in 2- and 4-, 2- and 5-, or 3- and 4-positions.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, propenyl isopropenyl, 2-butenyl, 3-methyl-2-butenyl, 2-pentenyl, 3-pentenyl, 2-hexenyl, 4-hexenyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The new 1-(disubstituted phenoxy)-3-amino-2-hydroxypropanes of the present invention and their condensation products with aldehydes, ketones or carbonic acid are obtained by several processes.

(a) Compounds of the formula:

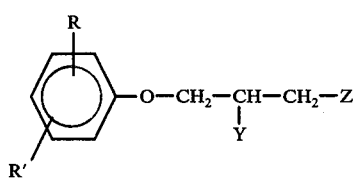
III in which
R and R' are as defined above,
Y is hydroxy and
Z is a reactive ester, or
Y and Z together are an epoxy group
are allowed to react with diphenylmethylamine or fluorenylamine (or a condensation product thereof with an aldehyde or ketone of the formula:

R''—N=X in which
R'' and X are as defined above).

By a reactive ester is intended a group derived from a hydroxy group by reaction with a strong inorganic or organic acid, in particular a hydrogen halide acid such as hydrochloric acid, hydrobromic acid or hydriodic acid, in which case Z is chloro, bromo or iodo, and sulfuric acid, or a strong aliphatic or aromatic sulfonic acid, for example methanesulfonic acid, benzenesulfonic acid, 4-bromobenzenesulfonic acid or 4-toluenesulfonic acid.

(b) An amine of the formula:

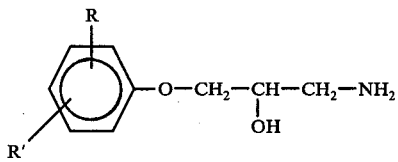
IV in which
R and R' are as defined above,
is allowed to react with a compound of the formula Z—R''
in which
Z and R'' are as defined above.

In lieu of the amine of Formula IV a condensation product thereof with an aldehyde or ketone of the formula:

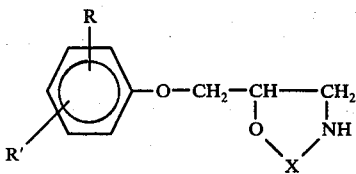
V in which
R, R' and X are as defined above or the corresponding condensation product with carbonic acid, of the formula:

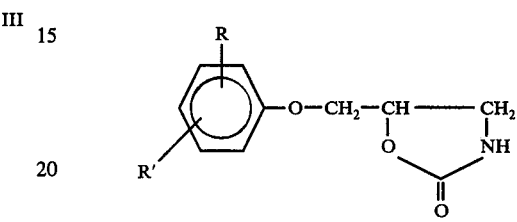
VA in which
R and R' are as defined above, can be used.

(c) A disubstituted phenol of the formula:

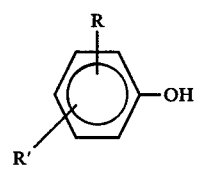
VI in which
R and R' are as defined above
is allowed to react with a compound of the formula:

Z—CH$_2$—CH—CH$_2$—NH—R''
          |
          Y

VII in which
R'', Y and Z are as defined above
or with the corresponding condensation product thereof with an aldehyde or ketone of the formula:

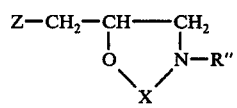
VIII in which
R'', X and Z are defined above,
or with a corresponding condensation product with carbonic acid of the formula:

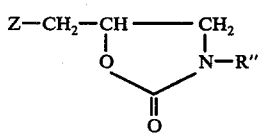
VIIIA in which
R'' and Z are as defined above.

(d) A compound of Formula I,
in which R, R' and R'' have the above meanings, but which carries a removable protecting group on either or both of the nitrogen atom of the 3-amino group and on the 2-hydroxy group, is appropriately treated to remove this group.

The compounds thus prepared can be converted in the customary manner into their physiologically tolerated acid addition salts. Suitable acids are, for example, hydrochloric acid, hydrobromic acid, sulfuric acid, phosphoric acid, methanesulfonic acid, acetic acid, lactic acid, succinic acid, maleic acid, fumaric acid, malic and tartaric acid.

The condensation products of the compounds are those with aldehydes and ketones, preferably with alkanals with up to 4 carbon atoms, particularly formaldehyde, or also with phenyl alkanals, particularly benzaldehyde (so that X is lower alkylidene or phenyl lower alkylidene), and those with carbonic acid. The compounds which are not condensed with aldehydes ketones or carbonic acid are preferred as therapeutic groups.

Protecting groups which are removable are those which can be split off by solvolysis, in particular by hydrolysis or ammonolysis. Those which can be split off by hydrolysis are, for example, acyl radicals, including functionally modified carboxyl groups, as for example oxycarbonyl groups, such as alkoxycarbonyl groups, e.g., the tert.-butoxycarbonyl or ethoxycarbonyl; aralkoxycarbonyl groups, such as phenyl lower alkoxycarbonyl radicals, e.g., carbobenzoxy and halogenocarbonyl groups such as chlorocarbonyl; arylsulphonyl groups, such as the toluenesulphonyl or bromobenzenesulphonyl group, lower alkanoyl groups, optionally halogenated as with fluorine such as formyl, acetyl or trifluoroacetyl; benzoyl; cyano; silyl groups, such as trimethylsilyl; and an acetal group. For the hydroxy group, the oxycarbonyl; lower alkanoyl; and benzoyl groups are preferred. For the amino group, ylidene groups can also be employed, as for example an alkylidene, benzylidene or phosphorylidene group, such as the triphenylphosphorylidene group, in which case the nitrogen atom then carries a positive charge.

In addition both the amino and hydroxy group can be protected. In addition to the condensation products already disclosed, a compound of the formula:

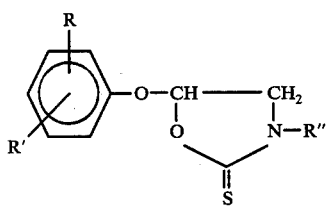

VIIIB wherein
R, R' and R" are as defined above, can thus be hydrolyzed to yield the free hydroxy aminopropanes.

Groups which can be split off by ammonolysis include, in particular, the halogenocarbonyl function, such as chlorocarbonyl.

If, in process embodiment (1), (2-ethoxy-5-propenylphenoxymethyl)-oxirane, or, in process embodiment a(2), 1-(2-ethoxy-5-propenylphenoxy)-2-hydroxy-3-chloropropane, and fluorenylamine are selected as typical starting materials, the reaction can be represented as follows:

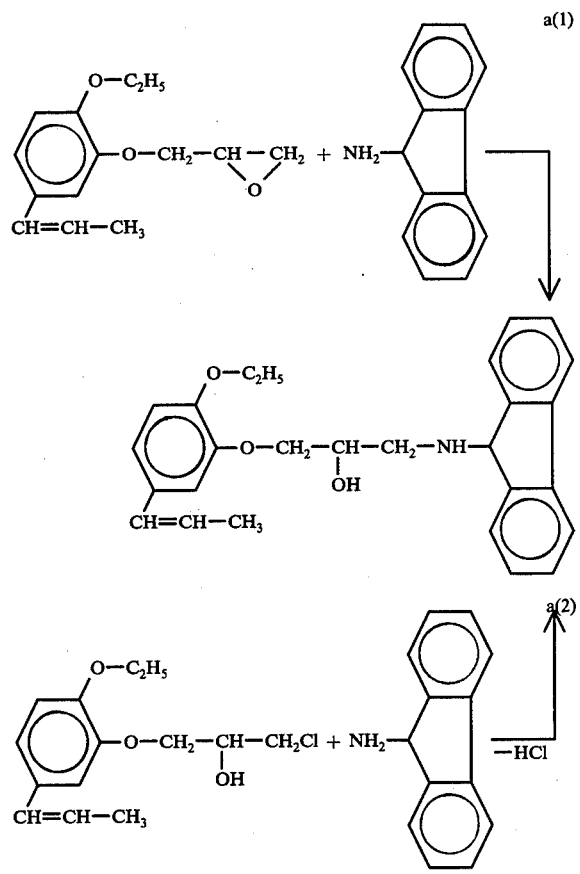

If, in process embodiment b), 1-(2-methoxy-4-allylphenoxy)-2-hydroxy-3-aminopropane and diphenylmethyl bromide are selected as typical starting materials, the reaction can be diagrammatically represented as follows:

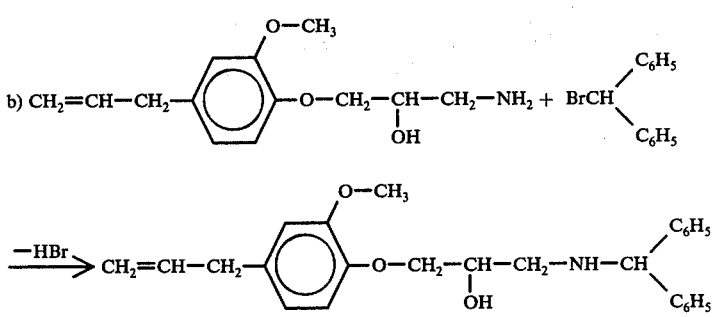

If, in process embodiment c(1), 1-chloro-2-hydroxy-3-diphenylmethylaminopropane, or, in process embodiment c(2), 2-methoxy-4-n-propylphenol diphenylaminomethyloxirane, and in both cases 2-methoxy-4-n-propylphenol are selected as typical starting materials, the reaction can be diagrammatically represented as follows:

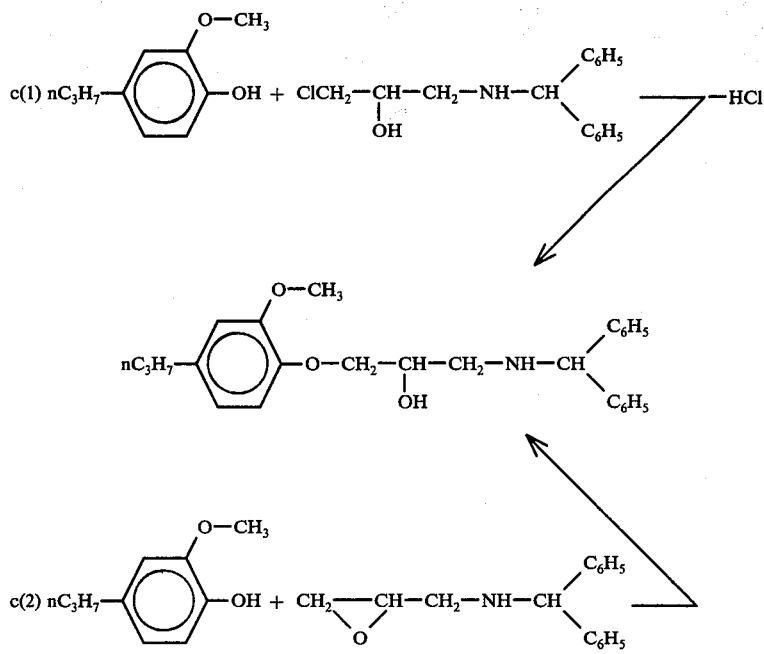

If, in process embodiment c(3), 2-methoxy-4-n-propylphenol and 3-diphenylmethyl-5-chloromethyloxazolidine are selected as typical starting materials, the reaction can be diagrammatically represented as follows:

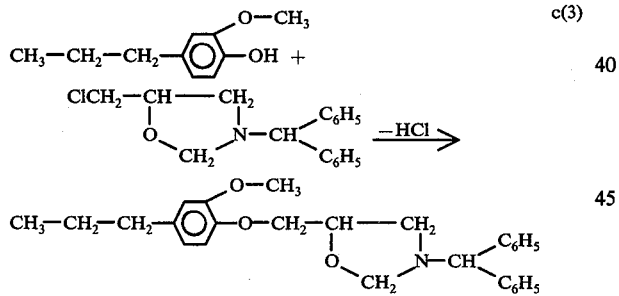

If, in process embodiment d), 1-(3,4-dichlorophenoxy)-2-hydroxy-3-(N-acetyldiphenylmethylamino)propane is selected as a typical starting material, the reaction can e diagrammatically represented as follows:

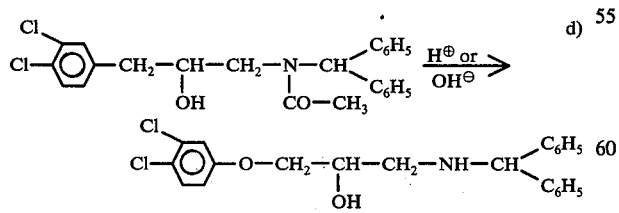

Alternatively in process embodiment d), if 1-(2-ethoxy-5-propenylphenoxy)-2-(tetrahydropyran-2-yloxy)-3-diphenylmethylaminopropane is selected as a representative starting material, the reaction can be diagrammatically represented as follows:

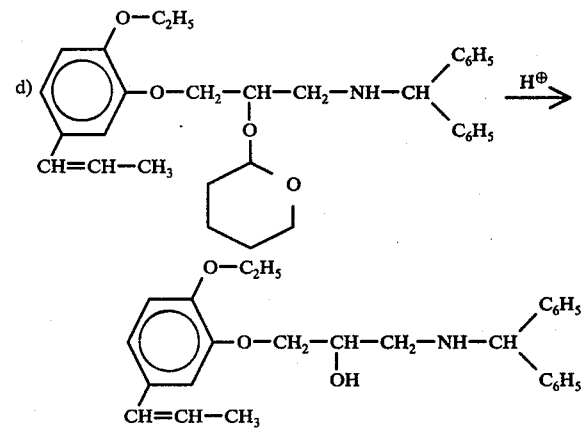

Finally in process embodiment d), if 3-diphenylmethyl-5-(2,4-dichlorophenoxymethyl)-oxazolidin-2-one is selected as the starting material, the reaction can be diagrammatically represented as follows:

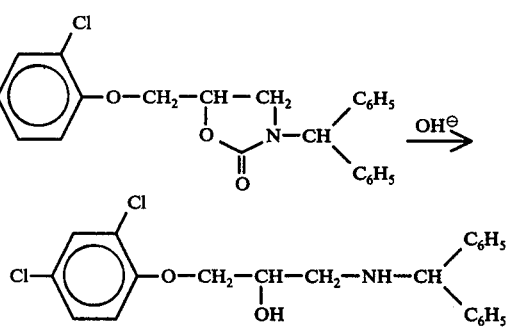

Some of the disubstituted phenol ethers of Formula III are known. Those which are new can be obtained by conventional techniques. Compounds of Formula III in which Y and Z form an epoxy group can thus be obtained by reacting the correspondingly disubstituted phenols of Formula VI with epichlorohydrin in the presence of at least molar amounts of a basic condensing agent. Disubstituted phenol ethers of Formula III in which Y is a hydroxy group and Z is a reactive ester group, such as for example chlorine, can be obtained from corresponding epoxides of Formula III by reaction with the appropriate acid, as for example hydrochloric acid. Disubstituted phenols of Formula VI also can be reacted with epichlorohydrin in the presence of catalytic amounts of a base, such as for example piperidine.

Typical starting materials of Formula III: (2-methyl-3-chlorophenoxymethyl)-oxirane, (2-methoxy-4-propyl-phenoxymethyl)-oxirane, (2-methoxy-4-allyl-phenoxymethyl)-oxirane,(2-methoxy-4-cis- and -4-trans-propenyl-phenoxymethyl)-oxirane, (2-carbethoxy-4-methoxy-phenoxymethyl)-oxirane, (2-carbethoxy-4-ethoxy-phenoxymethyl)-oxirane, (2,4-dichlorophenoxymethyl)-oxirane, (2-ethoxy-4-carbethoxy-phenoxymethyl)-oxirane, (2-methoxy-4-carbomethoxy-phenoxymethyl)-oxirane, (2-methoxy-4-chloro-phenoxymethyl)-oxirane, (2-ethoxy-4-chloro-phenoxymethyl)-oxirane, (2-allyl-4-methoxy-phenoxymethyl)-oxirane, (2-allyl-4-chloro-phenoxymethyl)-oxirane, (2-chloro-4-ethoxyphenoxymethyl)-oxirane, (2-ethoxy-5-propyl-phenoxymethyl)-oxirane, (2-methoxy-cis- and -5-trans-propenyl-phenoxymethyl)-oxirane, (2-ethoxy-5-cis- and -5-trans-propenylphenoxymethyl)-oxirane, (2,5-dichloro-phenoxymethyl)-oxirane, (2,5-diethoxy-phenoxymethyl)-oxirane, (2-methoxy-5-carbethoxy-phenoxymethyl)-oxirane, (2-ethoxy-5-carbethoxy-phenoxymethyl)-oxirane, (2-carbethoxy-5-methoxy-phenoxymethyl)-oxirane, (2-methoxy-5-chloro-phenoxymethyl)-oxirane, (2-ethoxy-5-chloro-phenyoxymethyl)-oxirane, (2-chloro-5-ethoxy-phenoxymethyl)-oxirane, (2,6-dimethyl-phenoxymethyl)-oxirane, (2-chloro-6-allyl-phenoxymethyl)-oxirane, (2-methoxy-6-allyl-phenoxymethyl)-oxirane, (2-ethoxy-6-allyl-phenoxymethyl)-oxirane, (2-methyl-6-chloro-phenoxymethyl)-oxirane, (2,6-dimethoxy-phenoxymethyl)-oxirane, (3,4-dichlorophenoxymethyl)-oxirane, (3,4-dimethoxy-phenoxymethyl)-oxirane, (3-chloro-4-methoxy-phenoxymethyl)-oxirane, (3-ethoxy-4-chloro-phenoxymethyl)-oxirane, (3-methyl-5-ethyl-phenoxymethyl)-oxirane, 1-(2-methyl-3-chloro-phenoxy)-2-hydroxy-3-chloropropane, 1(2-methoxy-4-propyl-phenoxy)-2-hydroxy-3-bromopropane, 1-(2-methoxy-4-allyl-phenoxy)-2-hydroxy-3-chloropropane, 1-(2-methoxy-4-cis- and -4-trans-propenylphenoxy)-2-hydroxy-3-chloropropane, 1-(2-carbethoxy-4-methoxy-phenoxy)-2-hydroxy-3-bromopropane, 1-(2-carbethoxy-4-ethoxy-phenoxy)-2-hydroxy-3-bromopropane, 1-(2,4-dichlorophenoxy)-2-hydroxy-3-iodopropane, 1-(2-ethoxy-4-carbethoxy-phenoxy)-2-hydroxy-3-chloropropane, 1-(2-methoxy-4-carbomethoxy-phenoxy)-2-hydroxy-3-chloropropane, 1-(2-methoxy-4-chloro-phenoxy)-2-hydroxy-3-chloropropane, 1-(2-ethoxy-4-chloro-phenoxy)-2-hydroxy-3-methanesulphonyloxypropane, 1-(2-allyl-4-methoxy-phenoxy)-2-hydroxy-3-benzenesulphonyloxypropane, 1-(2-allyl-4-chloro-phenoxy)-2-hydroxy-3-chloropropane, 1-(2-chloro-4-ethoxy-phenoxy)-2-hydroxy-3-toluenesulphonyloxy-propane, 1-(2-ethoxy-5-propyl-phenoxy)-2-hydroxy-3-iodopropane, 1-(2-methoxy-5-cis- and -5-trans-propenylphenoxy)-2-hydroxy-3-iodopropane, 1-(2-ethoxy-5-cis- and -5-trans-propenyl-phenoxy)-2-hydroxy-3-bromopropane, 1-(2,5-dichlorophenoxy)-2-hydroxy-3-chloropropane, 1-(2,5-diethoxyphenoxy)-2-hydroxy-3-chloropropane, 1-(2-methoxy-5-carbethoxyphenoxy)-2-hydroxy-3-chloropropane, 1-(2-ethoxy-5-carbethoxyphenoxy)-2-hydroxy-3-bromopropane, 1-(2-carbethoxy-5-methoxyphenoxy)-2-hydroxy-3-chloropropane, 1-(2-methoxy-5-chlorophenoxy)-2-hydroxy-3-chloropropane, 1-(2-ethoxy-5-chlorophenoxy)-2-hydroxy-3-bromopropane, 1-(2-chloro-5-ethoxyphenoxy)-2-hydroxy-3-bromopropane, 1-(2,6-dimethyl-phenoxy)-2-hydroxy-3-iodopropane, 1-(2-chloro-6-allyl-phenoxy)-2-hydroxy-3-chloropropane, 1-(2-methoxy-6-allyl-phenoxy)-2-hydroxy-3-chloropropane, 1-(2-ethoxy-6-allyl-phenoxy)-2-hydroxy-3-methanesulfulphonyloxypropane, 1-(2-methyl-6-chlorophenoxy)-2-hydroxy-3-benzenesulphonyloxypropane, 1-(2,6-dimethyl-phenoxy)-2-hydroxy-3-chloropropane, 1-(3,4-dichlorophenoxy)-2-hydroxy-3-toluenesulphonyloxypropane, 1-(3,4-dimethoxyphenoxy)-2-hydroxy-3-iodopropane, 1-(3-chloro-4-methoxy-phenoxy)-2-hydroxy-3-bromopropane, 1-(3-ethoxy-4-chloro-phenoxy)-2-hydroxy-3-chloro-propane and 1-(3-methyl-5-ethyl-phenoxy)-2-hydroxy-3-chloropropane.

Many of the amines of Formula IV are known. Those which are not can be readily obtained, in a simple manner, by reacting corresponding epoxides of Formula III with ammonia in an autoclave. Typical of the starting materials of Formula IV include: 1-(2-methyl-3-chlorophenoxy)-2-hydroxy-3-aminopropane, 1-(2-methoxy-4-propyl-phenoxy)-2-hydroxy-3-aminopropane, 1-(2-methoxy-4-allyl-phenoxy)-2-hydroxy-3-aminopropane, 1-(2-methoxy-4-cis- and -4-trans-propenyl-phenoxy)-2-hydroxy-3-aminopropane, 1-(2-carbethoxy-4-methoxy-phenoxy)-2-hydroxy-3-aminopropane, 1-(2-carbethoxy-4-ethoxy-phenoxy)-2-hydroxy-3-aminopropane, 1-(2,4-dichloro-phenoxy)-2-hydroxy-aminopropane, 1-(2-ethoxy-4-carbethoxy-phenoxy)-2-hydroxy-3-aminopropane, 1-(2-methoxy-4-carbomethoxyphenoxy)-2-hydroxy-3-aminopropane, 1-(2-methoxy-4-chlorophenoxy)-2-hydroxy-3-aminopropane, 1-(2-ethoxy-4-chlorophenoxy)-2-hydroxy-3-aminopropane, 1-(2-allyl-4-methoxyphenoxy)-2-hydroxy-3-aminopropane, 1-(2-allyl-4-chlorophenoxy)-2-hydroxy-3-aminopropane, 1-(2-chloro-4-ethoxyphenoxy)-2-hydroxy-3-aminopropane, 1-(2-ethoxy-5-propylphenoxy)-2-hydroxy-3-aminopropane, 1-(2-methoxy-5-cis- and -5-trans-propenyl-phenoxy)-2-hydroxy-3-aminopropane, 1-(2-ethoxy-5-cis- and -5-trans-propenyl-phenoxy)-2-hydroxy-3-aminopropane, 1-(2,5-dichloro-phenoxy)-2-hydroxy-3-aminopropane, 1-(2,5-diethoxy-phenoxy)-2-hydroxy-3-aminopropane, 1-(2-methoxy-5-carbethoxy-phenoxy)-2-hydroxy-3-aminopropane, 1-(2-ethoxy-5-carbethoxyphenoxy)-2-hydroxy-3-aminopropane, 1-(2-carbethoxy-5-methoxy-phenoxy)-2-hydroxy-3-aminopropane, 1-(2-methoxy-5-chloro-phenoxy)-2-hydroxy-3-aminopropane, 1-(2-ethoxy-5-chloro-phenoxy)-2-hydroxy-3-aminopropane, 1-(2-chloro-5-ethoxy-phenoxy)-2-hydroxy-3-amino-propane, 1-(2,6-dimethyl-phenoxy)-2-hydroxy-3-aminopropane, 1-(2-chloro-6-allyl-phenoxy)-2-hydroxy-3-aminopropane, 1-(2-methoxy-6-allyl-phenoxy)-2-hydroxy-3aminopropane, 1-(2-ethoxy-6-allyl phenoxy)-2-hydroxy-3-aminopropane, 1-(2-methyl-6-chlorophenoxy)-2-hydroxy-3-aminopropane, 1-(2,6-dimethoxyphenoxy)-2-hydroxy-3-aminopropane, 1-(3,4-dichloro-phenoxy)-2-hydroxy-3-aminopropane, 1-(3,4-dimethoxy-phenoxy)-2-hydroxy-3-aminopropane, 1-(3-chloro-4-methoxy-phenoxy)-2-hydroxy-3-aminopropane, 1-(3-ethoxy-4-chloro-phenoxy-2- hydroxy-3-aminopropane and 1-(3-methyl-5-ethyl-phenoxy)-2-hydroxy-3-aminopropane.

Likewise the amines of Formula VII are known in many cases or can be prepared according to known processes. Compounds of Formula VII in which Y is hydroxy and Z is a reactive ester, for example chloro, can be obtained by the reaction of diphenylmethylamine or fluorenylamine with epichlorohydrin. Hydrogen chloride can be eliminated from these new 1-chloro-2-hydroxy-3-diphenylmethylamino- [or -9-fluorenylamino)-] propanes in a known manner by means of strong base to yield diphenylmethylaminomethyl- and 9-fluorenylaminomethyloxiranes. Generally these need not be isolated but can be further processed as crude products.

The compounds in which hydroxy and/or amino are protected result from the customary process modification in which a desired protective group(s) is introduced at a preliminary stage of the synthesis of starting materials for utilized process embodiments a through c. Typical of such protected compounds are 1-(2-methoxy-4-propyl-phenoxy)-2-tetrahydropyran-2-yloxy)-3-diphenylmethyl-aminopropane, 1-(2-methoxy-4-propyl-phenoxy)-2-acetoxy-3-diphenylmethylaminopropane, N-acetyl-3-(2-methoxy-4-propyl-phenoxy)-2-hydroxy-1-diphenylmethylaminopropane, 2-phenyl-3-diphenylmethyl-5-(2-methoxy-4-propyl-phenoxy-methyl)-oxazolidine, 3-diphenylmethyl-5-(2-methoxy-4-propyl-phenoxy-methyl)-oxazolidin-2-one, 1-(2-methoxy-4-allyl-phenoxy)-2-(tetrahydropyran-2-yloxy)-3-diphenylaminopropane, 1-(2-methoxy-4-allyl-phenoxy)-2-propionyloxy-3-diphenylmethylaminopropane, N-acetyl-1-(2-methoxy-4-allyl-phenoxy)-2-hydroxy-3-diphenylmethylaminopropane, 2-methyl-3-diphenyl-methyl-5-(2-methoxy-4-allyl-phenoxy-methyl)-oxazolidine, 3-diphenylmethyl-5-(2-methoxy-4-allyl-phenoxy-methyl)-oxazolidin-2-one, 1-(2-ethoxy-5-trans-propenyl-phenoxy)-2-(tetrahydropyran-2-yloxy)-3-diphenylmethylaminopropane, 1-(2-ethoxy-5-trans-propenyl-phenoxy)-2-(tetrahydropyran-2-yloxy)-3-(9-fluorenylamino)-propane, 1-(2-ethoxy-5-transpropenyl-phenoxy)-2-acetoxy-3-diphenylmethylaminopropane, 1-(2-ethoxy-5-trans-propenyl-phenoxy)-2-propionyloxy-3-(9-fluorenylamino)-propane, N-acetyl-1-(2-ethoxy-5-trans-propenyl-phenoxy)-2-hydroxy-3-diphenylmethylaminopropane, N-acetyl-1-(2-ethoxy-5-trans-propenyl-phenoxy)-2-hydroxy-3-(9-fluorenylamino)-propane, 2-methyl-3-diphenylmethyl-5-(2-ethoxy-5-trans-propenyl-phenoxy-methyl)-oxazolidine, 2-methyl-3-(9-fluorenyl)-5-(2-ethoxy-5-trans-propenyl-phenoxymethyl)-oxazolidine, 2-phenyl-3-diphenyl-methyl-5-(2-ethoxy-5-trans-propenyl-phenoxy-methyl)-oxazolidine, 2-phenyl-3-(9-fluorenyl)-5-(2-ethoxy-5-trans-propenyl-phenoxy-methyl)-oxazolidine, 3-diphenylmethyl-5-(2-ethoxy-5-trans-propenyl-phenoxymethyl)-oxazolidin-2-one, 3-(9-fluorenyl)-5-(2-ethoxy-5-trans-propenyl-phenoxymethyl)-oxazolidin-2-one, 3-(3,4-dichloro-phenoxy)-2-(tetrahydropyran-2-yloxy)-1-diphenylmethylaminopropane, 3-(3,4-dichloro-phenoxy)-2-acetoxy-1-diphenylmethylaminopropane, N-acetyl-3-(3,4-dichloro-phenoxy)-2-hydroxy-1-diphenylmethylaminopropane, 2-phenyl-3-diphenylmethyl-5-(3,4-dichloro-phenoxymethyl)-oxazolidine and 3-diphenyl-methyl-5-(3,4-dichloro-phenoxymethyl)-oxazolidin-2-one.

In process embodiment a(1), generally molar amounts of the reactants are allowed to react in a diluent. Diluents which can be used are all inert organic solvents, as for example, hydrocarbons such as ligroin and toluene, ethers such as diethyl ether, glycol dimethyl ether and dioxane; alcohols such as methanol, ethanol and isopropanol; glycol monomethyl ether and halogenated hydrocarbons such as chloroform, methylene chloride and the like. The reaction temperatures can be varied within a relatively wide range generally from 20° C to 120° C and preferably from 60° C to 100° C. The reaction can be carried out under elevated pressure, but preferably is carried out under normal pressure. When the reaction has ended, the solution is concentrated in vacuo, preferably to about half of its volume. In some cases, the free base will crystallize from the concentrated reaction solution upon cooling. If not, the solution is rendered acidic to Congo Red with ethereal hydrochloric acid, the sparingly soluble hydrochloride salt crystallizing out and being further purified by recrystallization.

Process embodiments a(2), b and c(3) are carried out in substantially the same fashion, however in the presence of a basic condensing agent, as for example alkali metal hydroxides, such as sodium hydroxide or potassium hydroxide, alkali metal carbonates, such as potassium carbonate, and alkali metal alcoholates, such as sodium methylate, potassium ethylate and potassium tert.-butylate. The reaction is carried out at a temperature of from 60° C to 200° C especially from 100° C to 130° C, and preferably under such pressure that, depending on the boiling point of the diluent used, the preferred reaction temperature is reached. When the reaction has ended, the inorganic salts are removed by filtration and the resulting amines collected as described above.

In process embodiment c(1), again molar amounts of the reactants are employed in a diluent, here however in the presence of an acid-binding agent. The diluents include those discussed above, particularly hydrocarbons, ethers, alcohols, glycol monomethyl ether and ketones such as acetone, methyl isobutyl ketone and cyclohexanone. The acid-binding agents are the customary agents of this type such as alkali metal alcoholates such as sodium methylate and sodium ethylate; alkali metal hydroxides such as sodium hydroxide and potassium hydroxide; and alkali metal carbonates such as sodium carbonate and potassium carbonate. The reaction is carried out at a temperature of from 30° C to 200° C and preferably from 50° C to 100° C. Again the reaction can be carried out under elevated pressure but is preferably carried out under normal pressure. After the reaction has ended, the insoluble inorganic salts are filtered off and the reaction solution is concentrated as discussed above.

In process embodiment c(2), molar amounts of the reactants are preferably reacted directly. A diluent can be used, as discussed above, but the reaction is generally conducted without a diluent. The reaction temperatures will range from 50° C to 150° C, preferably from 70° C to 120° C, preferably under normal pressure. When the reaction is complete, the reaction mixture is dissolved, if necessary, in a suitable diluent and the product collected as discussed above.

Hydrolysis of protecting groups in process embodiment d) utilizes either acid agents such as dilute mineral acids or basic agents such as of alkali metal hydroxides. Oxycarbonyl, arylsulphonyl and cyano groups are generally split off with the aid of acidic agents such as a hydrogen halide acid, appropriately hydrobromic acid and preferably dilute hydrobromic acid optionally mixed with acetic acid. Cyano groups are preferably split off with hydrobromic acid at elevated temperature, such as in boiling hydrobromic acid (the Braun bromocyano method). A tert.-butoxycarbonyl group can be removed under anhydrous conditions by treatment with a suitable acid such as trifluoroacetic acid.

Ammonolysis is effected in the customary manner, such as for example, with an amine which contains at least one hydrogen atom bonded to the nitrogen atom, such as with a mono- or di-(lower alkyl)amine, as for example, methylamine or dimethylamine, or in particular with ammonia, and is preferably effected at elevated temperature. In place of ammonia, it is also possible to use an agent which releases ammonia, such as hexamethylenetetramine.

Depending on the choice of the starting materials and the procedures, the new compounds can be in the form of enantiomers or racemates or, if they contain at least two centres of chirality, in the form of mixtures of diastereomeric racemates. In those cases in which the new compounds contain an alkenyl with different substituents about the double bond, it is also possible for geometric isomers, or their mixtures, to exist. Mixtures of diastereomeric racemates and of geometric isomers can be resolved into the two pure diastereomeric racemates or, respectively, separated into the cis- and trans-isomers in a known manner on the basis of the physicochemical differences between the constituents, for example by chromatography and/or fractional crystallization. Resulting racemates can be resolved into the enantiomers by known methods, for example by recrystallization from an optically active solvent, with the aid of micro-organisms or by reaction with an optically active acid which forms salts with the racemic compound and separation of the diastereomers obtained in this way, for example on the basis of their different solubilities. The enantiomers are then liberated from the diastereomers by conventional methods. Optically active acids which are particularly commonly used are, for example, the D- and L- forms of tartaric acid, di-o-toluyltartaric acid, malic acid, mandeli acid, camphorsulfonic acid and quinic acid.

The compounds according to the invention increase the mental functional capacity, the cerebral blood flow and the resistance of the brain to transitory total ischaemia. They are therefore indicated in the case of reduced intellectual functional capacity with age and for trauma and especially for the prophylaxis and therapy of apoplectic shocks.

There is thus provided a method of combatting the above-mentioned conditions in humans and other animals, by which a compound of the invention, alone or in admixture, is administered perorally, parenterally (for example intramuscularly, intraperitoneally or intravenously) or rectally, preferably parenterally and especially intravenously.

In general, significant effects are observed upon administering the compounds in amounts of from about 0.1 to about 10.0 mg/kg, preferably 0.5 to 5.0 mg/kg, of body weight every 24 hours. Optionally this is in the form of several individual administrations, in order to achieve the desired results. An individual administration can for example contain from about 0.05 to about 5.0 mg/kg, and especially 0.1 to 1.0 mg/kg, of body weight. However, the dose must be titrated to the condition and response and it may be necessary to depart from the precise dosages mentioned and in particular to do so as a function of the age, nature and body weight of the patient, the nature and the severity of the condition, the formulation, the route of administration, and frequency of administration, in all cases utilizing sound professional judgment.

Compared with currently available cerebral therapeutic agents such as pemoline, bencyclan, vincamine, cinnarizin, piracetam and xanthinol niacinate, the compounds of the invention display a considerably stronger and longer-lasting activity. Surprisingly, the new substances do not display any blocking or stimulating action on the adrenergic $\beta$-receptors of the various organs, nor do they have any antihistaminic action.

These pharmacological actions can be conveniently observed in recognized animal models of which the following are representative for a number of typical compounds.

In the representative data which follow, the compounds of the invention are abbreviated as follows: 1-(2-ethoxy-5-trans-propenylphenoxy)-2-hydroxy-3-diphenylmethylaminopropane hydrochloride of Example 1 is "compound A"; 1-(2-methoxy-4-allylphenoxy)-2-hydroxy-3-diphenylmethylaminopropane hydrochloride of Example 4 is "compound B"; 1-(2-ethoxy-5-trans-propenylphenoxy)-2-hydroxy-3-(9-fluorenylamino)-propane of Example 28 is "compound C" and 1-(3,4-dichlorophenoxy)-2-hydroxy-3-diphenylmethylaminopropane of Example 26 is "compound D." In addition, the following commercially available products were included for purposes of comparison: 1-isopropylamino-3-(1-naphthyloxy)-2-propanol (= propanolol) as $\beta$-blocking agent, and bencyclan, 1-cinnamyl-4-diphenylmethylpiperazin (= cinnarizin) and vincamine as cerebral therapeutic agents.

1. Protective action against amnesia in male mice

Method

A modification of the method of Taber and Banuazizi (Psychopharmacol. 9, 382–91, 1966) was employed.

Mice are taught to remain seated in a small compartment of a test cage and not to move into the larger compartment in which an electric shock to the foot were previously received. If a convulsive electric shock is applied to a mouse after it has been so taught, it develops amnesia and forgets the previous experience (the shock to its foot in the larger compartment), and moves from the smaller compartment into the larger compartment. By pre-treating the animals with a test substance, it is possible to determine whether these substances have any protective action against the amnesia produced.

Each test substance is administered to the particular animal 3 times at intervals of 24 hours, the last administration being 1 hour before the first test. Two groups are formed for each test; a control group with amnesia and a pre-treated group.

For each test group, the average value of the times which have elapsed befoe the barrier is crossed on the 2nd day is calculated. This time is taken as a criterion for the learning capacity.

Figure 2:
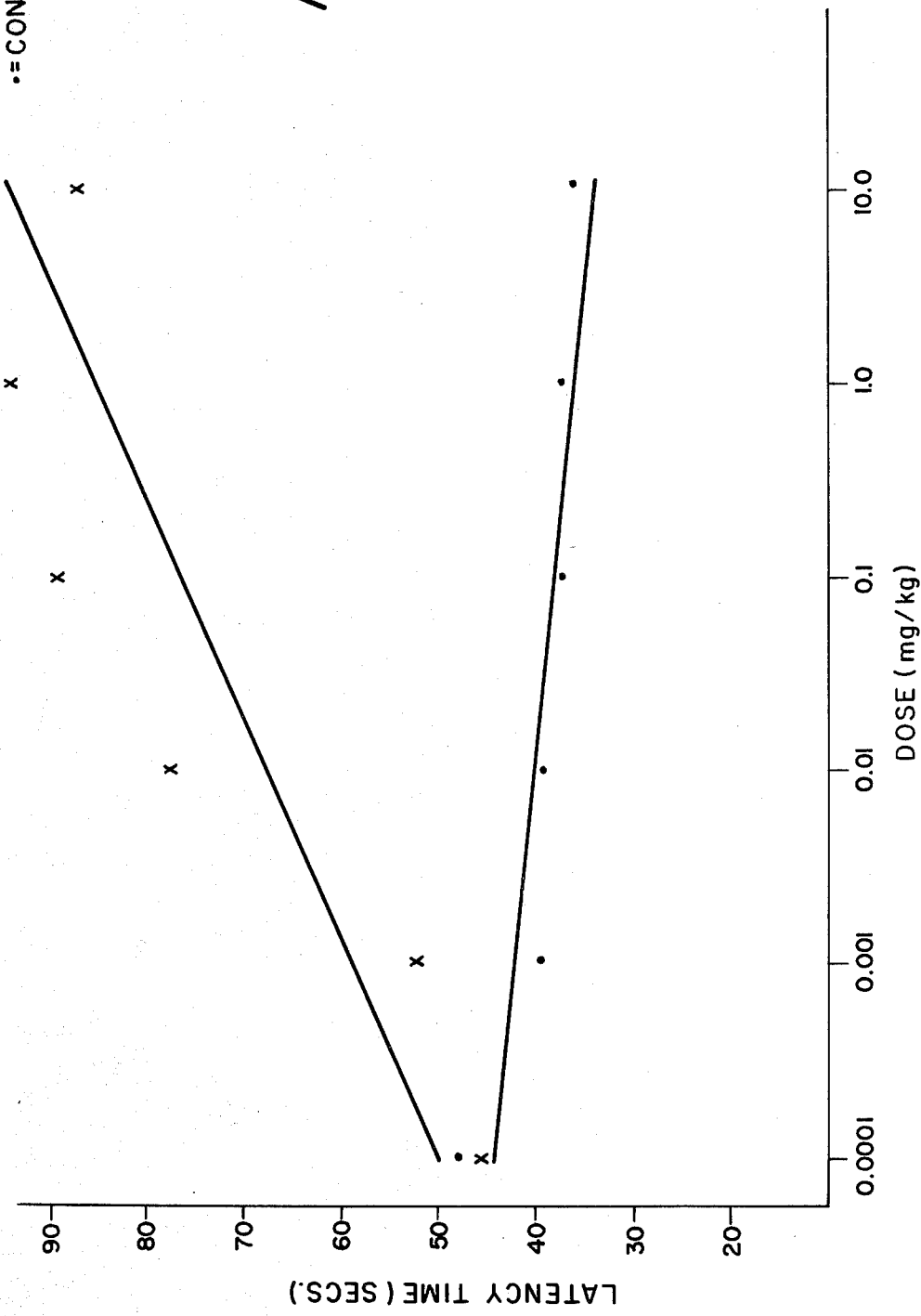
Figure 3:
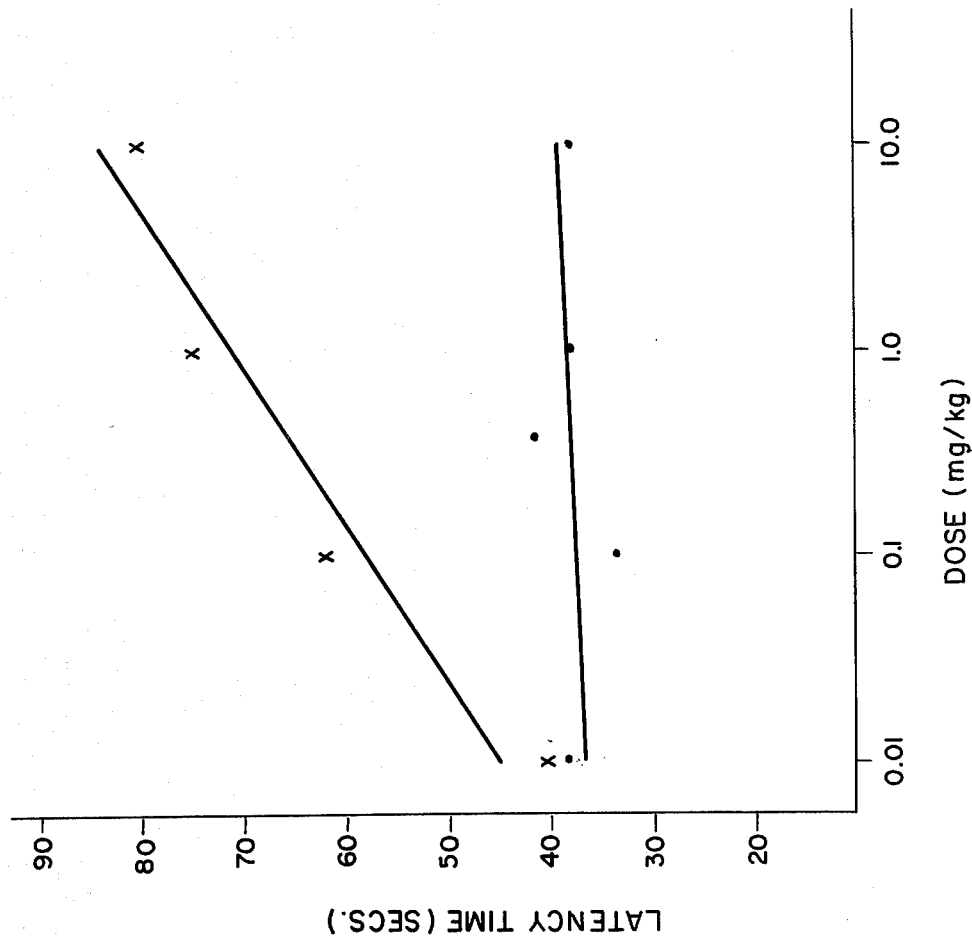
Figure 5:
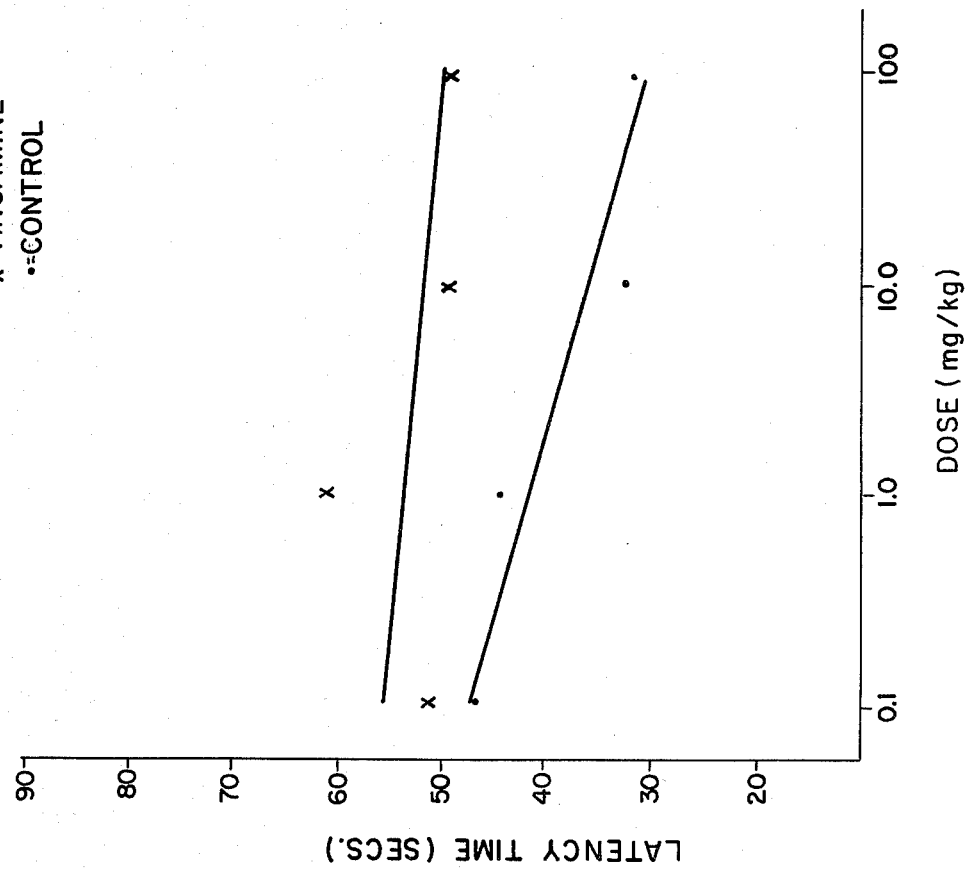
Figure 4:
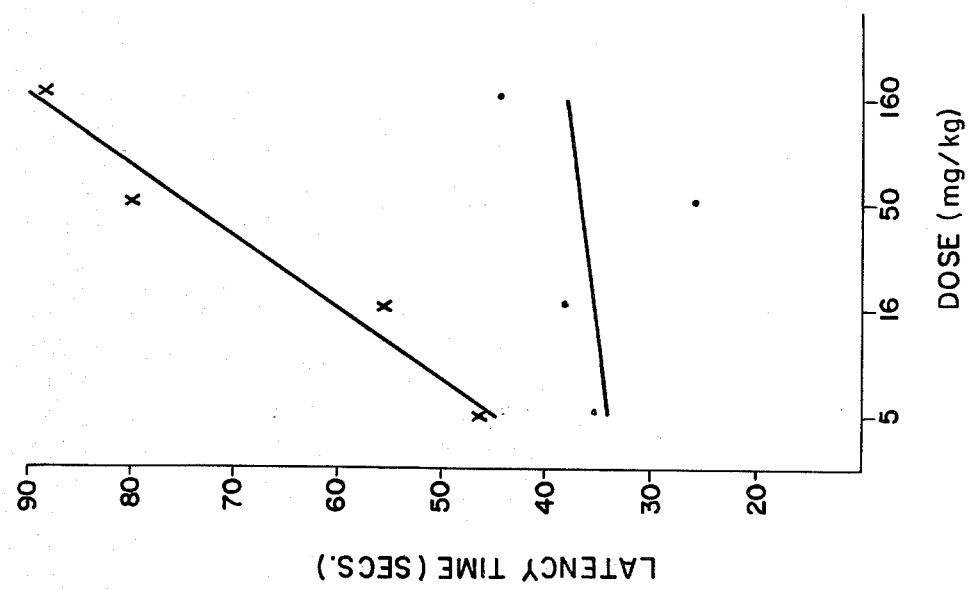

The results of the experiments are illustrated graphically in the accompanying drawings in which FIG. 1: shows the protective action of compound A against amnesia induced by electric shock in male mice;

FIG. 2: shows the protective action of compound B against amnesia induced by electric shock in male mice;

FIG. 3: shows the protective action of compound D against amnesia induced by electric shock in male mice;

FIG. 4: shows the protective action of propranolol against amnesia induced by electric shock in male mice; and FIG 5: shows the protective action of vincamine against amnesia induced by electric shock in male mice.

As can be seen from FIGS. 1–5, compounds A, B and D according to the invention are considerably more effective against amnesia induced by elctric shock in mice than the comparison substances propanolol and vincamine.

2. Increase in the cerebral blood flow in cats and dogs

Method

Cats (1.8–3.0 kg) and dogs (18–25 kg) of both sexes are rendered analgetic with fentanyl and curarized. The specific blood flow through the grey and white brain matter is determined with the aid of the clearance curve for $^{133}$xenon.

Table 1

| Substance | administration (cats) | |
|---|---|---|
| | Dose mg/kg | Increase in the cerebral blood flow by % |
| Compound A | 2.5 | 40 |
| Compound B | 10 | 48 |
| Compound C | 2.5 | 28 |
| Compound D | 2.5 | 77 |
| Bencyclan | 10 | 30 |
| Cinnarizin | 5 | 30 |
| Vincamine | 8 | 27 |

Table 2

| Substance | Oral administration (cats) | |
|---|---|---|
| | Dose mg/kg | Increase in the cerebral blood flow by % |
| Compound A | 50 | 12 |
| Compound B | 50 | 10 |
| Compound C | 25 | 30 |
| Compound D | 50 | 44 |
| Bencyclan | up to 50 | φ |
| Cinnarizin | up to 100 | φ |

Figure 6A:
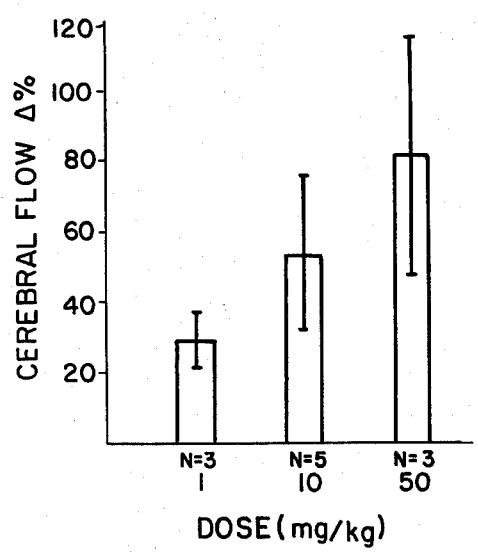
Figure 6B:
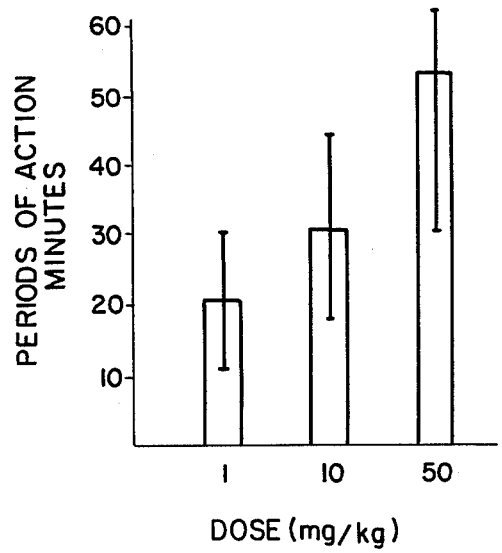
Figure 7:
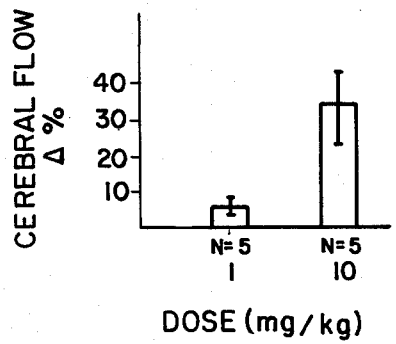

Results for compound A and bencyclan are graphically depicted in FIGS. 6A, 6B and 7.

As can be seen from Tables 1 and 2 and FIGS. 6A, 6B and 7, compounds A, B, C and D in this test significantly increase the cerebral blood flow in cats and dogs. On intravenous administration, their action at lower doses is stronger than that of the comparison substances. On peroral administration to cats, bencyclan and cinnarizin are inactive at 50 and 100 mg/kg respectively, while compounds A, B, C and D display a distinct action at 50 and 25 mg/kg.

3. Restricted circulation and mortality after a transient total cerebral ischaemia ("experimental apoplexy")

Method

A 7-minute complete cerebral ischaemia is caused in curarized cats by inflating a collar placed around the neck. The blood flow (measured by $^{133}$xenon clearance), initially increses when the cerebral circulatory system is opened again but falls within a few minutes to far below the initial vale and does not reach this value again, even after hours.

For cats which have not been pre-treated, the 7-minute cerebral ischaemia is fatal, 94% of all the control animals dying within 48 hours.

The compounds according to the invention however have a significant protective action against this nonreflow phenomenon. In the case of cats which were pretreated with compound A (50 mg/kg perorally), no restriction in the cerebral blood flow occurs after a 7-minute cerebral ischaemia. Only 33% of the cats pretreated with compound A died, the difference being significant at $p > 0.01$. The compounds not only increase the blood supply in a healthy brain but have a distinct prophylactic and therapeutic action in an extreme experimental apoplexy.

The comparison substances, vincamine and cinnarizin, ae inactive in this test.

General pharmacology and toxicology of these compounds can be summarized as follows. At a concentration of about $10^{-1}$ mg/ml, the compounds have a positive inotropic action on an isolaed guinea-pig atrium. The compounds however are not $\beta$-sympathomimetic agents since this action is not eliminated by $\beta$-blocking agents. A $\beta$-sympatholytic action can also be excluded since the $\beta$-sympathomimetic action of isoproterenol is not influenced by the compounds. Since the spasm caused in an isolated intestine by histamine is not specifically inhibited, the compounds do not have antihistamine action.

Typical values for acute toxicity ($LD_{50}$) in mice are as follows:

Table 3

| Compound | $LD_{50}$ (mg/kg) | |
|---|---|---|
| | Intravenously | Orally |
| A | 80 | >2,000 |
| B | 43 | 450 |
| C | 85 | >2,000 |
| D | 76 | >2,000 |
| propranolol | 30 | 220 |
| bencyclan | 33 | >2,000 |
| cinnarizin | 27 | >2,000 |
| vincamine | 95 | 460 |

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alterantive to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insolbule.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

Suppositories can be formulated from the usual water-soluble or water-insoluble diluents, such as polyethylene glycols and fats, e.g. cocoa oil and high esters such as those of $C_{14}$-alcohol with $C_{16}$-fatty acid or mixtures of these diluents.

For parenteral administration, the solutions and emulsions will be course be sterile, and, if appropriate, blood-isotonic.

All the pharmaceutical compositions according to the invention can also contain coloring agents and preservatives as well as perfumes and flavoring additions (e.g. peppermint oil and eucalyptus oil) and sweentening agents (e.g. saccharin). They will generally contain from 0. to 99.5%, more usually from 0.5 to 95%, of the active ingredient by weight of the total composition.

In addition to a compound of the invention, the compositions can contain other pharmaceutically active compounds, as well as a plurality of compounds of this invention.

The examples which follow will serve to further illustrate the inventionn without being a limitation on the scope thereof. The temperatures are given in degrees Celsius.

EXAMPLE 1 (process a,l)

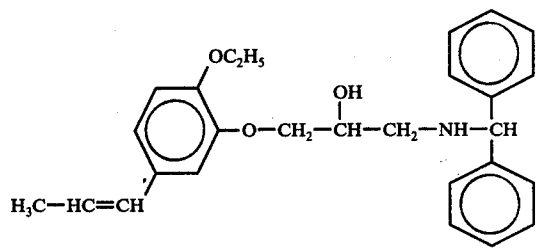

117 g of (2-ethoxy-5-trans-propenyl-phenoxymethyl)-oxirane are dissolved in 400 ml of isopropanol. After adding 91.5 g of diphenylmethylamine, the mixture is heated for 5 hours under a reflux condenser. After cooling, the resulting reaction solution is concentrated in vacuo to approximately half its original volume and is rendered acid to Congo Red with ethereal hydrochloric acid. After the further addition of dry ether, 166 g (= 73% of theory) of 1-(2-ethoxy-5-transpropenyl-phenoxy)-2-hydroxy-3-diphenylmethylaminopropane hydrochloride crystallizes out in the form of colorless crystals which, after recrystallization from a methanol/water mixture, melt at 145°–146°.

The crystalline base which is obtainable from this product with aqueous ammonia melts, after recrystallization from petroleum ether, at 75°–76°.

(2-Ethoxy-5-trans-propenyl-pehnoxymethyl)-oxirane which has a melting point of 68°–69° and is required as the starting material is obtained by reacting 4-propengylguaethol with epichlorohydrin in aqueous potassium hydroxide solution.

The compounds which follow are prepared according to the process of Example 1:

EXAMPLE 2

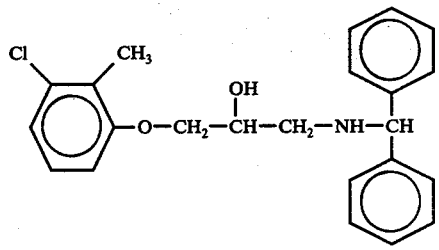

66.1 g = 79% of theory of 1-(2-methyl-3-chlorophenoxy)-2-hydroxy-3-diphenylmethylaminopropane hydrochloride from 39.7g of (2-methyl-3-chlorophenoxymethyl)-oxirane (boiling point $_{0.45}$ 120°–123° C) and 36.6 g of diphenylmethylamine. Colorless crystals with a melting point of 207°–210° (from methanol).

EXAMPLE 3

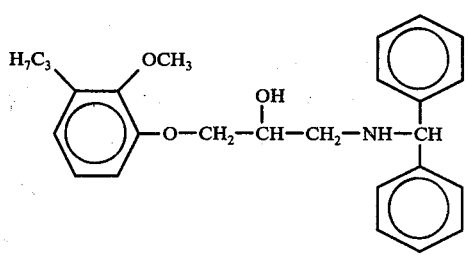

21.9 g = 82.5% of theory of 1-(2-methoxy-4-n-propylphenoxy)-2-hydroxy-3-diphenylmethylaminopropane hydrochloride from 13.3 g of (2-methoxy-4-n-propyl-phenoxymethyl)-oxirane (melting point 41°–43°) and 11 g of diphenylmethylamine. Colorless crystals with a melting poit of 108°–110° C (from ethyl acetate/petroleum ether).

EXAMPLE 4

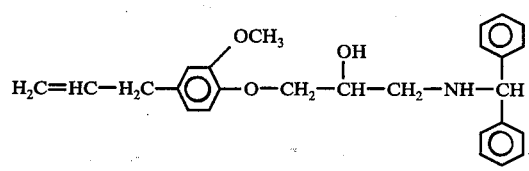

53.2 g = 80.6% of theory of 1-(2-methoxy-4-allyl-phenoxy)-2-hydroxy-3-diphenylmethylaminopropane hydrochloride from 33.0 g of (2-methoxy-4-allyl-phenoxymethyl)-oxirane (melting point 37°–38.5°) and 27.4 g of diphenylmethylamine. Colorless crystals with a melting point 143° (from methanol/water).

EXAMPLE 5

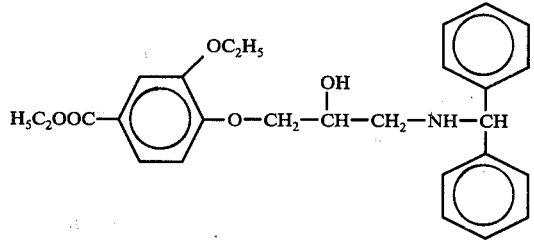

21 g = 72% of theory of 1-(2-ethoxy-4-carbethoxy-phenoxy)-2-hydroxy-3-diphenylmethylaminopropane hydrochloride from 16 g of (2-ethoxy-4-carbethoxy-phenoxymethyl)-oxirane (melting point 59°–61°) and 11 g of diphenylmethylamine. Colorless crystals with a melting point of 148°–150° (from isopropanol).

EXAMPLE 6

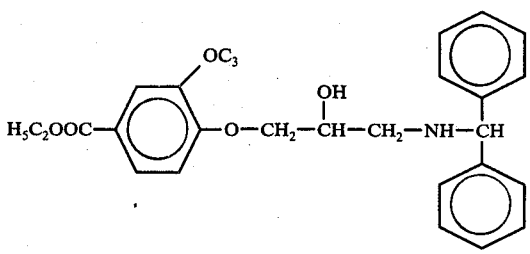

37.3 g = 75.2% of theory of 1-(2-methoxy-4-carbomethoxyphenoxy)-2-hydroxy-3-diphenylmethylaminopropane hydrochloride from 26.4 g of (2-methoxy-4-carbethoxy-phenoxymethyl)-oxirane (melting point 79°–81°) and 19.2 g of diphenylmethylamine. Colorless crystals with a melting point of 143°–146° C (from ethanol/water).

EXAMPLE 7

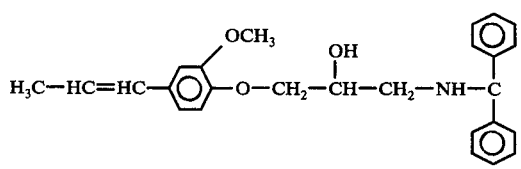

35 g = 87.4% of theory of 1-(2-methoxy-4-cis-propenylphenoxy)-2-hydroxy-3-diphenylmethylaminopropane hydrochloride from 20 g of (2-methoxy-4-cis-propenyl-phenoxymethyl)-oxirane (boiling point $_{0.5}$ 148°–152°) and 16.7 g of diphenylmethylamine. Colorless crystals with a melting point of 133°–136°.

EXAMPLE 8

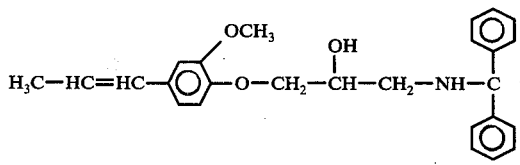

46.7 g = 78% of theory of 1-(2-methoxy-4-trans-propenylphenoxy)-2-hydroxy-3-diphenylmethylaminopropane hydrochloride from 30 g of (2-methoxy-4-trans-propenyl-phenoxymethyl)-oxirane (melting point 55°–58°) and 24.9 g of diphenylmethylamine. Colorless crystals with a melting point of 129°–132° (from isopropanol/ether).

EXAMPLE 9

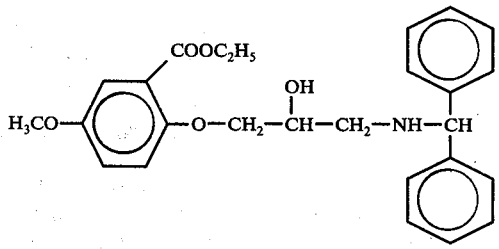

44.2 g = 89% of theory of 1-(2-carbethoxy-4-methoxy-phenoxy)-2-hydroxy-3-diphenylmethylaminopropane hydrochloride from 26.5 g of (2-carbethoxy-4-methoxy-phenoxymethyl)-oxirane (boiling point$_{0.05}$ 169°–170°) and 19.2 g of diphenylmethylamine. Colorless crystals with a melting point of 120°–124°.

EXAMPLE 10

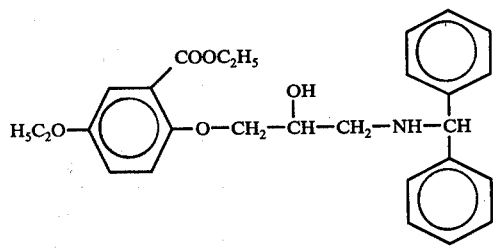

16.4 g = 61.4% of theory of 1-(2-carbethoxy-4-ethoxy-phenoxy)-2-hydroxy-3-diphenylmethylaminopropane hydrochloride from 14.6 g of (2-carbethoxy-4-ethoxy-phenoxymethyl)-oxirane (boiling point$_{0.7}$ 184°–188°) and 10 g of diphenylmethylamine. Colorless crystals with a melting point of 182°–184°.

EXAMPLE 11

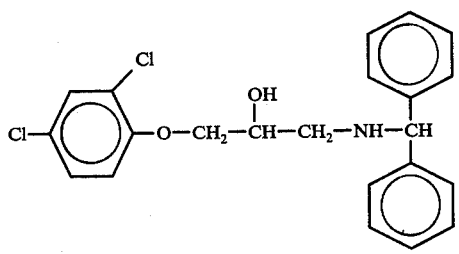

29.4 g = 73.1% of theory of 1-(2,4-dichloro-phenoxy)-2-hydroxy-3-diphenylmethylaminopropane hydrochloride from 21.9g of (2,4-dichloro-phenoxy-methyl)-oxirane (boiling point$_{0.1}$ 140°–145°) and 18.3 g of diphenylmethylamine. Colorless crystals with a melting pont of 226°–228°.

EXAMPLE 12

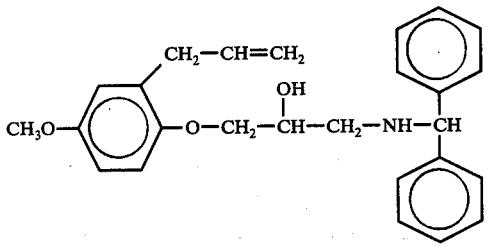

55.1 g = 83.5% of theory of 1-(2-allyl-4-methoxy-phenoxy)-2-hydroxy-3-diphenylmethylaminopropane hydrochloride from 33 g of (2-allyl-4-methoxy-phenoxymethyl)-oxirane (boiling point$_{0.05}$ 117°–122°) and 27.5 g of diphenylmethylamine. Colorless crystals with a melting point of 157°–159°.

EXAMPLE 13

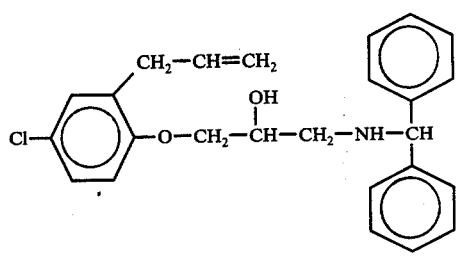

44.7 g = 67% of theory of 1-(2-allyl-4-chloro-phenoxy)-2-hydroxy-3-diphenylmethylaminopropane hydrochloride from 33.7 g of (2-allyl-4-chloro-phenoxymethyl)-oxirane (boiling point$_{0.07}$ 122°–124°) and 27.5 g of diphenylmethylamine. Colorless crystals with a melting point of 157°–158° C (from methanol/water).

EXAMPLE 14

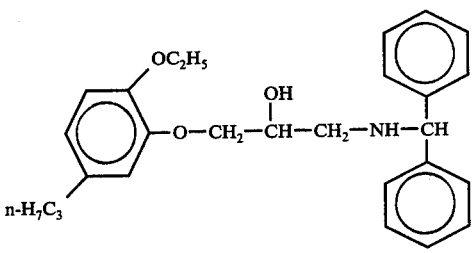

18.8 g = 68.7% of theory of 1-(2-ethoxy-5-n-propyl-phenoxy)-2-hydroxy-3-diphenylmethylaminopropane hydrochloride from 14.2 g of (2-ethoxy-5-n-propyl-phenoxymethyl)-oxirane (boiling point $_{0.6}$ 148°–154°, melting point 48°–52°) and 11 g of diphenylmethylamine. Colorless crystals with a melting point of 111°–113° (from isopropanol/ether).

EXAMPLE 15

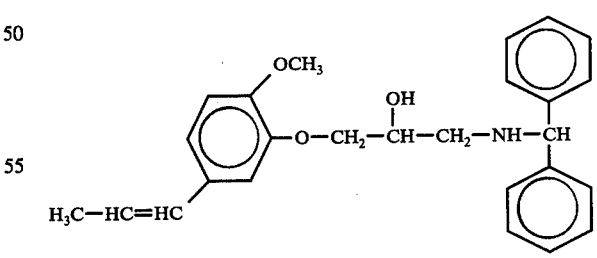

37.9 g = 86% of theory of 1-(2-methoxy-5-trans-propenylphenoxy)-2-hydroxy-3-diphenylmethylaminopropane hydrochloride from 22 g of (2-methoxy-5-trans-propenyl-phenoxymethyl)-oxirane (boiling point$_{0.3}$ 146°–151°, melting point 58°–59°) and 18.3g of diphenylmethylamine. Colorless crystals with a melting point of 163°–165° (from ethanol).

EXAMPLE 16

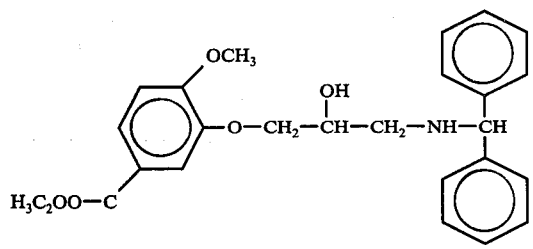

23.5 g = 83% of theory of 1-(2-methoxy-5-carbethoxyphenoxy)-2-hydroxy-3-diphenylmethylaminopropane hydrochloride from 15.1 g of (2-methoxy-5-carbethoxy-phenoxymethyl)-oxirane (boiling point$_{0.25}$ 160°–167°, melting point 61°–63° from ligroin) and 11 g of diphenylmethylamine. Colorless crystals with a melting point of 175°–177° (from ethanol).

EXAMPLE 17

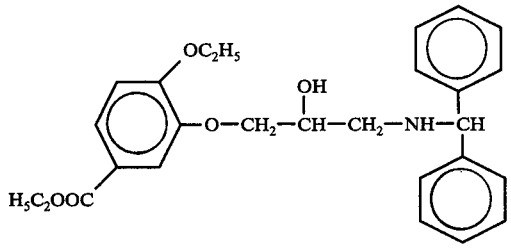

36.3 g = 74.7% of theory of 1-(2-ethoxy-5-carbethoxyphenoxy)-2-hydroxy-3-diphenylmethylaminopropane hydrochloride from 26.6 g of (2-ethoxy-5-carbethoxy-phenoxymethyl)-oxirane (boiling point$_{0.6}$ 185°–188°, melting point 40°–43°) and 18.3g of diphenylmethylamine. Colorless crystals with a melting point of 185°–187° from ethanol.

EXAMPLE 18

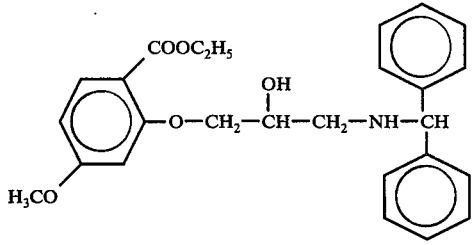

31.2 g = 69.6% of theory of 1-(2-carbethoxy-5-methoxy-phenoxy)-2-hydroxy-3-diphenylmethylaminopropane hydrochloride from 24 g of (2-carbethoxy-5-methoxyphenoxymethyl)-oxirane (boiling point$_{0.1}$ 165°–172°) and 17.4g of diphenylmethylamine. Colorless crystals with a melting point of 167°–171° (from isopropanol).

EXAMPLE 19

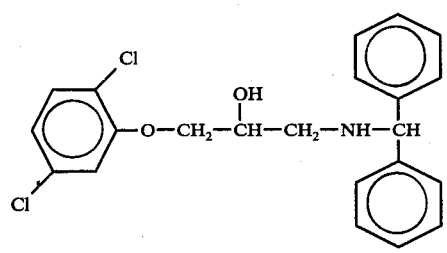

21.5 g = 76.9% of theory of 1-(2,5-dichlorophenoxy)-2-hydroxy-3-diphenylmethylaminopropane hydrochloride from 15.2 g of (2,5-dichloro-phenoxymethyl)-oxirane (boiling point$_{0.1}$ 133°–139°, melting point 65°–66° from methanol) and 12.7 g of diphenylmethylamine.

Colorless crystals with a melting point of 74°–76.5° (from methanol).

EXAMPLE 20

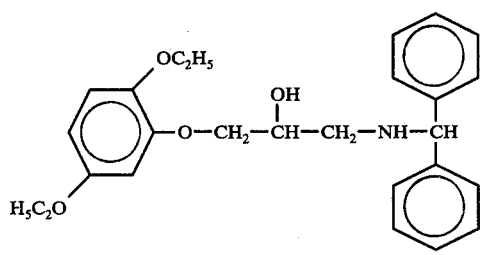

23 g = 83.7% of theory of 1-(2,5-diethoxy-phenoxy)-2-hydroxy-3-diphenylmethylaminopropane hydrochloride from 14.3 g of (2,5-diethoxy-phenoxymethyl)-oxirane (boiling point$_{0.04}$ 145°–150°, melting point 32°–34°) and 11g of diphenylmethylamine. Coloress crystals with a melting point of 131°–133°.

EXAMPLE 21

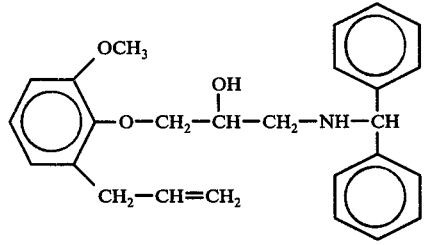

48.6 g = 73.6% of theory of 1-(2-methoxy-6-allyl-phenoxy)-2-hydroxy-3-diphenylmethylaminopropane hydrochloride from 33.0 g of (2-methoxy-6-allyl-phenoxymethyl)-oxirane (boiling point$_{0.05}$ 114°–121°) and 27.4 g of diphenylmethyl-amine. Colorless crystals with a melting point of 167°–170° (from methanol/water).

EXAMPLE 22

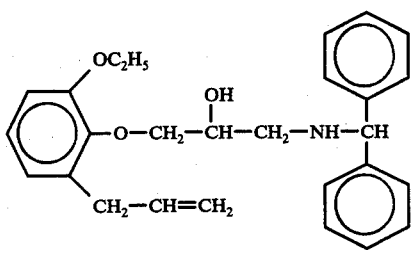

44.8 g = 65.8% of theory of 1-(2-ethoxy-6-allyl-phenoxy)-2-hydroxy-3-diphenylmethylaminopropane hydrochloride from 35.1 g of (2-ethoxy-6-allyl-phenoxymethyl)-oxirane (boiling point$_{0.08}$ 120°–127°) and 27.5 g of diphenylmethylamine. Colorless crystals with a melting point of 136°–138° (from isopropanol/ether).

EXAMPLE 23

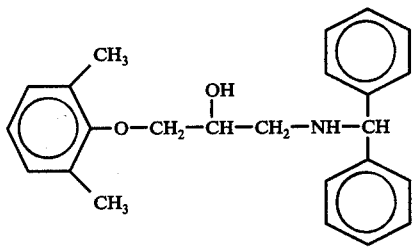

43.5 g = 72.9% of theory of 1-(2,6-dimethyl-phenoxy)-2-hydroxy-3-diphenylmethylaminopropane hydrochloride from 26.7 g of (2,6-dimethyl-phenoxymethyl)-oxirane (boiling point$_{0.07}$ 90°–94°) and 27.5 g of diphenylmethylamine. Colorless crystals with a melting point of 161°–164° (from isopropanol).

EXAMPLE 24

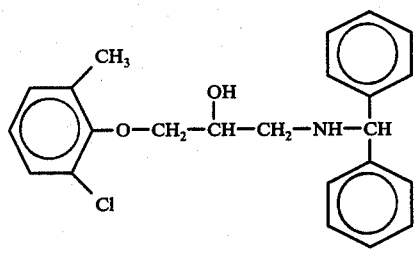

30 g = 82.8% of theory of 1-(2-methyl-6-chloro-phenoxy)-2-hydroxy-3-diphenylmethylaminopropane hydrochloride from 17.1 g of (2-methyl-6-chloro-phenoxymethyl)-oxirane (boiling point$_{0.5}$ 104°–113°) and 15.8 g of diphenylmethylamine. Colorless crystals with a melting point of 170°–172° (from methanol/water).

EXAMPLE 25

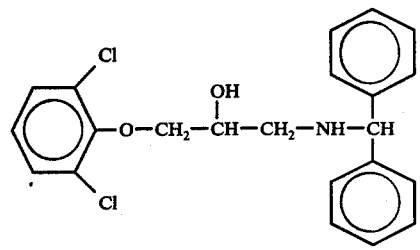

30.1 g = 68.7% of theory of 1-(2,6-dichloro-phenoxy)-2-hydroxy-3-diphenylmethylaminopropane hydrochloride from 21.9g of (2,6-dichloro-phenoxymethyl)-oxirane (boiling point$_{0.1}$ 142°–148°) and 18.3 g of diphenylmethylamine. Colorless crystals with a melting point of 185°–188° (from methanol/water).

EXAMPLE 26

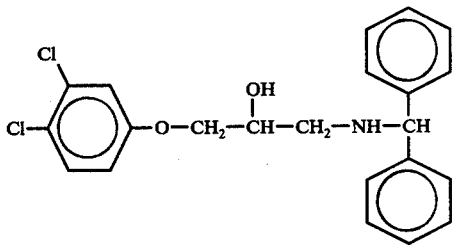

38.1 g (86.1% of theory) of 1-(3,4-dichloro-phenoxy)-2-hydroxy-3-diphenylmethylaminopropane from 24.1 g of (3,4-dichloro-phenoxymethyl)-oxirane (boiling point$_{0.1}$ 145°–150°, melting point 42°–43° from methanol) and 20.1 g of diphenyl-methylamine; the said product crystallizes out as the free base when the reaction solution is evaporated. Colorless crystals with a melting point of 114°–115° (from methanol).

EXAMPLE 27

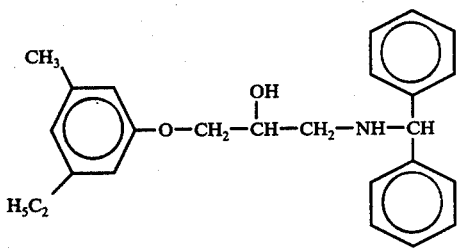

70.5 g = 85.6% of theory of 1-(3-methyl-5-ethyl-phenoxy)-2-hydroxy-3-diphenylmethylaminopropane hydrochloride from 38.4 g of (3-methyl-5-ethyl-phenoxymethyl)-oxirane (boiling point$_{0.1}$ 115°–120°) and 36.6 g of diphenylmethylamine. Colorless crystals with a melting point of 142.5°–145.5° (from methanol/water).

EXAMPLE 28

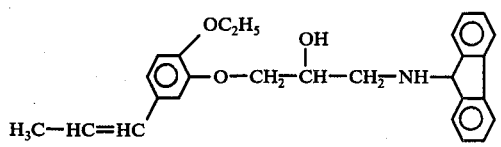

93.4 g (69.1% of theory) of 1-(2-ethoxy-5-trans-propenyl-phenoxy)-2-hydroxy-3-(9-fluorenylamino)-propane from 76.2 g of (2-ethoxy-5-trans-propenyl-phenoxymethyl)-oxirane and 59 g of 9-aminofluorene; and said product crystallizes out as the free base when the reaction solution is cooled. Colorless crystals with a melting point of 119°–121° (from isopropanol).

EXAMPLE 29

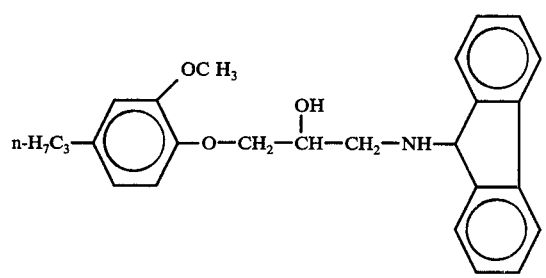

27.8 g = 69% of theory of 1-(2-methoxy-4-n-propyl-phenoxy)-2-hydroxy-3-(9-fluorenylamino)-propane with a melting point of 85°–88° from 22.2 g of (2-methoxy-4-n-propyl-phenoxy-methyl)-oxirane and 18.1 g of 9-aminofluorene.

EXAMPLE 30

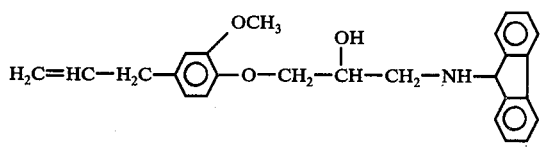

30.3 g = 75.4% of theory of 1-(2-methoxy-4-allyl-phenoxy)-2-hydroxy-3-(9-fluorenylamino)-propane with a melting point of 120°–122° from 22 g (2-methoxy-4-allyl-phenoxymethyl)-oxirane and 18.1 g of 9-aminofluorene.

EXAMPLE 31

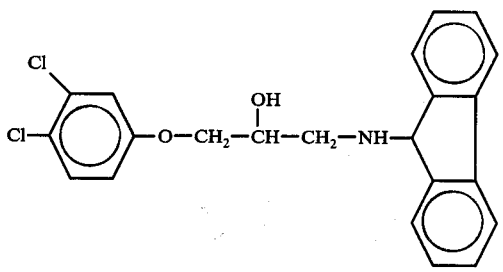

35.4 g = 81.1% of theory of 1-(3,4-dichloro-phenoxy)-2-hydroxy-3-(9-fluorenylamino)-propane with a melting point of 156°–159° from 21.9 g of (3,4-dichlorophenoxymethyl)-oxirane and 18.1 g of 9-aminofluorene.

EXAMPLE 32

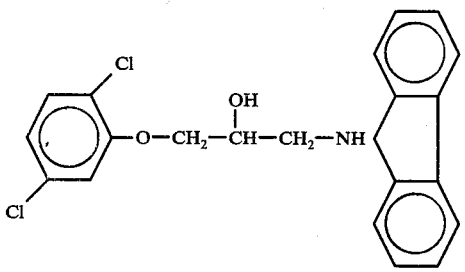

34 g = 77.9% of theory of 1-(2,5-dichloro-phenoxy)-2-hydroxy-3-(9-fluorenylamino)-propane with a melting point of 93°–95° from 21.9 g iof (2,5-dichloro-phenoxymethyl)-oxirane and 18.1 g of 9-aminofluorene.

EXAMPLE 33 (process a,2)

200 ml of epichlorohydrin and 0.5 ml of piperidine are added to 17.8 g of 4-trans-propenylguaethol and the mixture is then heated to 100° for 10 hours. The excess epichlorohydrin is then distilled off in vacuo and the residue is dissolved in 50 ml of isopropanol. After adding 18.3 g of diphenylmethylamine and 30 g of potassium carbonate, the mixture is heated to 120° in an autoclave for 10 hours. After the reaction has ended, the inorganic salts are filtered off and the resulting reaction solution is rendered acid to Congo Red with ethereal hydrochloric acid. 1-(2-Ethoxy-5-trans-propenyl-phenoxy)-2-hydroxy-3-diphenylaminopropane hydrochloride then crystallizes out; after recrystallization from a methanol/water mixture this melts at 145°–146° and is identical to the product described in Example 1. Yield: 16.3 g = 35.9% of theory of colorless crystals.

The compounds which follow are prepared according to the process described in Example 33:

EXAMPLE 34

12.4 g = 29.8% of theory of 1-(2-ethoxy-5-propenyl-phenoxy)-2-hydroxy-3-(9-fluorenylamino)-propane from 17.8 g of 4-trans-propenylguaethol, 200 ml of epichlorohydrin, 0.5 g of piperidine and 18.1 g of 9-aminofluorene; the product crystallizes out of the resulting reaction solution in the cold. Colorless crystals with a melting point of 119°–121° which are identical to the produce described in Example 28.

EXAMPLE 35

10.9 g = 24.8% of theory of 1-(2-methoxy-4-allyl-phenoxy)-2-hydroxy-3-diphenylmethylaminopropane hydrochloride from 16.4 g of eugenol, 200 ml of epichlorohydrin, 0.5 g of piperidine and 18.3 g of diphenylmethylamine. The colorless crystals which have a melting point of 143° are identical to the product described in Example 4.

EXAMPLE 36

13.3 g = 30.1% of theory of 1-(2-methoxy-4-n-propyl-phenoxy)-2-hydroxy-3-diphenylmethylaminopropane hydrochloride from 16.6 g of 2-methoxy-4-n-propyl-phenol, 200 ml of epichlorohydrin, 0.5 g of piperidine and 18.3 g of diphenylmethylamine. The colorless crystals which have a melting point of 108°–110° are identical to the product described in Example 3.

EXAMPLE 37

10.5 g = 26.1% of 1-(3,4-dichloro-phenoxy)-2-hydroxy-3-diphenylmethylaminopropane hydrochloride, in the form of colorless crystals with a melting point of 180°–184°, from 16.3 g of 3,4-dichlorophenol, 200 ml of epichlorohydrin, 0.5 ml of piperidine and 8.3 g of diphenylmethylamine. The free base, which is obtainable from this product and has a melting point of 114°–115°, is identical to the product described in Example 26.

EXAMPLE 38 (process b)

A solution of 22.2 g of (2-methoxy-4-n-propyl-phenoxy-methyl)-oxirane in 200 ml of isopropanol is saturated with gaseous ammonia and the mixture is then heated to 100° C in an autoclave for 4 hours, the resulting reaction solution is then evaporated to about half its original volume and, after adding 30 g of potassium carbonate and 20.2 g of diphenylmethylchloride, the mixture is heated to 120° for 10 hours. After the inorganic salts have been separated off, the resulting reaction solution is rendered acid to Congo Red with ethereal hydrochloric acid and 16.1 g = 36.4% of theory of 1-(2-methoxy-4-n-propyl-phenoxy)-2-hydroxy-3-diphenylmethylaminopropane hydrochloride are obtained. The colorless crystals melt at 108°–110° and are identical to the product described in Example 3.

The compounds which follow are prepared according to the process described in Example 38:

EXAMPLE 39

15.0 g = 34.1% of theory of 1-(2-methoxy-4-allyl-phenoxy)-2-hydroxy-3-diphenylmethylaminopropane hydrochloride from 22 g of (2-methoxy-4-allyl-phenoxymethyl)-oxirane, ammonia and 20.2 g of diphenylmethyl chloride. Colorless crystals which have a melting point of 143° and are identical to the product described in Example 4.

EXAMPLE 40

19.6 g = 43.1% of theory of 1-(2-ethoxy-5-propenyl-phenoxy)-2-hydroxy-3-diphenylmethylaminopropane hydrochloride from 23.4 g of (2-ethoxy-5-trans-propenyl-phenoxymethyl)-oxirane, ammonia and 20.2 g of diphenylmethyl chloride. Colorless crystals which have a melting point of 145°–146° and are identical to the product described in Example 1.

EXAMPLE 41

14.9 g = 35.9% of theory of 1-(2-ethoxy-5-trans-propenyl-phenoxy)-2-hydroxy-3-(9-fluorenylamino)-propane from 23.4 g of (2-ethoxy-5-trans-propenyl-phenoxymethyl)-oxirane, ammonia and 24.5 g of 9-bromofluorene. The free base is obtained direct if the organic salts are separated off while the mixture is still hot and the product is then allowed to crystallize out in the cold. The colorless crystals melt at 119°–121° and are identical to the product described in Example 28.

EXAMPLE 42

14.9 g of 1-(3,4-dichloro-phenoxy)-2-hydroxy-3-dipnenylmethylaminopropane from 21.9 g of (3,4-dichloro-phenoxymethyl)-oxirane, ammonia and 24.7 g of diphenylmethyl bromide; the product is obtained in the form of the free base if the reaction mixture is worked up as in Example 41. Yield: 37% of theory. Colorless crystals which have a melting point of 114°–115° and are identical to the product described in Example 26.

EXAMPLE 43 (process c,1)

17.8 g of 4-trans-propenylguaethol and 27.6 g of 3-diphenylmethylamino-2-hydroxy-1-chloropropane (melting point 66°–68°), which is obtained by reacting molar amounts of diphenylmethylamine and epichlorohydrin in isopropanol at 20°, are added to a solution of sodium ethylate prepared from 2.3g of sodium and 100 ml ethanol. The mixture is heated to 100° in an autoclave for 12 hours. The sodium chloride which has precipitated out is then filtered off and, by adding ethereal hydrochloric acid to the filtrate, 18.9 g = 41.6% of theory of 1-(2-ethoxy-5-trans-propenyl-phenoxy)-2-hydroxy-3-diphenylmethylaminopropane hydrochloride are obtained. The colorless crystals have a melting point of 145°–146° and are identical to the product described in Example 1.

The compounds which follow are prepared according to the process described in Example 43:

EXAMPLE 44

16.7 g = 37.8% of theory of 1-(2-methoxy-4-n-propyl-phenoxy)-2-hydroxy-3-diphenylmethylaminopropane hydrochloride from 16.6 g of 2-methoxy-4-n-propyl-phenol and 27.6 g of 1-diphenylmethylamino-2-hydroxy-3-chloropropane. Colorless crystals which have a melting point of 108°–110° and are identical to the product described in Example 3.

EXAMPLE 45

17.1 g = 38.9% of theory of 1-(2-methoxy-4-allyl-phenoxy)-2-hydroxy-3-diphenylmethylaminopropane hydrochloride from 16.4 g of eugenol and 27.6 g of 1-diphenylmethylamino-2-hydroxy-3-chloropropane. Colorless crystals which have a melting point of 143° and are identical to the product described in Example 4.

EXAMPLE 46

14.1 g (35% of theory) of 1-(3,4-dichloro-phenoxy)-2-hydroxy-3-diphenylmethylaminopropane from 16.3 g of 3,4-dichlorophenol and 27.6 g of 1-diphenylmethylamino-2-hydroxy-3-chloro-propane; the product crystallizes out as the free base when the reaction solution is evaporated. Colorless crystals which have a melting point of 114°–115° and are identical to the product described in Example 26.

EXAMPLE 47

2 ml of water are added to a solution of 18.1 g of 9-aminofluorene in 200 ml of methanol and 9.4 g of epichlorohydrin are then added dropwise at room temperature. The mixture is stirred overnight and then evaporated in vacuo at a bath temperature of 40°. The residue is added to a prepared solution of 2.3 g of sodium and 17.8 g of 4-trans-propenyl-guaethol in 100 ml of ethanol. The mixture is heated to 100° in an autoclave for 12 hours. The sodium chloride which has precipitated out is then filtered off and the filtrate is concentrated in vacuo to about half of the original volume. 9.8 g (=23.6% of theory) of 1-(2-ethoxy-5-trans-propenyl-phenoxy)-2-hydroxy-3-(9-fluorenylamino)propane crystallise out in the cold. Colorless crystals which have a melting point of 119°–121° and are identical to the product described in Example 28.

EXAMPLE 48 (process c,2)

27.6 g of 1-diphenylmethylamino-2-hydroxy-3-chloropropane are dissolved in 75 ml of 2 N methanolic sodium hydroxide solution. After the solution has stood at room temperature for one hour, the sodium chloride which has precipitated is filtered off and the filtrate is evaporated in vacuo at a bath temperature which is not above 30°. The oily residue is partitioned, by stirring, between 200 ml of ether and 50 ml of water. The layers are separated and the ethereal layer is washed twice more with, in each case, 50 ml of water and dried with potassium carbonate. After evaporating in vacuo (bath temperature $\leq$ 30°), 23.1 g of diphenylmethylaminomethyloxirane are obtained as a yellowish oil which is further processed as the crude product, without purification. 17.8g of 4-trans-propenylguaethol are added and the mixture is heated to 100° for 10 hours. The reaction mixture is then dissolved in 50 ml of isopropanol and the solution is acidified with ethereal hydrochloric acid.

22.4 g = 49.5% of theory of 1-(2-ethoxy-5-trans-propenylphenoxy)-2-hydroxy-3-diphenylmethylaminopropane hydrochloride are obtained. Colorless crystals which have a melting point of 145°–146° and are identical to the product described in Example 1.

The compounds which follow are prepared by the same process.

EXAMPLE 49

20.1 g = 45.7% of theory of 1-(2-methoxy-4-allyl-phenoxy)-2-hydroxy-3-diphenylmethylaminopropane hydrochloride from 27.6 g of 1-diphenylmethylamino-2-hydroxy-3-chloropropane and 16.4 g of eugenol. Colorless crystals which have a melting point of 143° and are identical to the product described in Example 4.

EXAMPLE 50

23.1 g = 52.3% of theory of 1-(2-methoxy-4-n-propylphenoxy)-2-hydoxy-3-diphenylmethylaminopropane hydrochloride from 27.6 g of 1-diphenylmethylamino-2-hydroxy-3-chloropropane and 16.6 g of 2-methoxy-4-n-propyl-phenol. Colorless crystals which have a melting point of 108°–110° and are identical to the product described in Example 3.

EXAMPLE 51

17.4 g = 43.2% of theory of 1-(3,4-dichloro-phenoxy)-2-hydroxy-3-diphenylmethylaminopropane from 27.6 g of 1-diphenylmethylamino-2-hydroxy-3-chloropropane and 16.3 g of 3,4-dichlorophenol; the product crystallizes out from the cooled reaction solution in the form of the free base. Colorless crystals which have a melting point of 114°–115° and are identical to the product described in Example 26.

EXAMPLE 52

18.1 g of 9-aminofluorene are reacted with epichlorohydrin, following the procedure described in Example 47, to give 1-(9-fluorenylamino)-2-hydroxy-3-chloropropane, from which, without purification, (9-fluorenylaminomethyl)oxirane is obtained with methanolic sodium hydroxide solution, by the procedure described in Example 48. Reaction of this compound with 17.8 g of 4-trans-propenylguaethol gives 16.1g = 38.7% of theory of 1-(2-ethoxy-5-trans-propenyl-phenoxy)-2-hydroxy-3-(9-fluorenylamino)-propane, which crystallizes out from the reaction solution in the cold in the form of the free base. Colorless crystals which have a melting point of 119°–121° and are identical to the product described in Example 28.

EXAMPLE 53 (process d)

9.6 g of dihydropyrane are added slowly dropwise to the 3-(2-ethoxy-5-trans-propenyl-phenoxy)-2-hydroxy-1-chloropropane, prepared according to Example 33 from 17.8 g of 4-trans-propenylguaethol, 200 ml of epichlorohydrin and 0.5 ml of piperidine, and a catalytic amount of p-toluenesulphonic acid. The mixture is warmed to 40° for 30 minutes and dissolved in 150 ml of isopropanol and 18.3g of diphenylmethylamine and 30 g of potassium carbonate are added. The resulting mixture is then heated to 120° in an autoclave for 10 hours.

After the reaction has ended, the inorganic salts are filtered off, 50 ml of hydrochloric acid are added to the filtrate and the mixture is warmed to 80° for 15 minutes. It is then evaporated to dryness in vacuo and the solid residue is recrystallized from methanol/water. This gives 17.5 g = 38.5% of theory of 1-(2-ethoxy-5-trans-propenyl-phenoxy)-2-hydroxy-3-diphenylaminopropane hydrochloride which has a melting point of 145°–146° and is identical to the product described in Example 1.

The compounds which follow are prepared according to the process described in Example 53:

EXAMPLE 54

1-(2-Methoxy-4-n-propyl-2-phenoxy)-2-hydroxy-3-diphenylmethylaminopropane hydrochloride, which has a melting point of 108°–110° and is identical to the product described in Example 3, from 1-(2-methoxy-4-n-propyl-phenoxy)-2-(tetrahydropyran-2-yloxy)-3-diphenylmethylaminopropane, which is not isolated.

EXAMPLE 55

1-(2-Methoxy-4-allyl-phenoxy)-2-hydroxy-3-diphenylmethylaminopropane hydrochloride, which has a melting point of 143° and is identical to the product described in Example 4, from 1-(2-methoxy-4-allyl-phenoxy)-2-(tetrahydropyran-2-yloxy)-3-diphenylmethylaminopropane, which is not isolated.

EXAMPLE 56

1-(3,4-Dichloro-phenoxy)-2-hydroxy-3-diphenylmethylaminopropane hydrochloride, which has a melting point of 180°–184° and is identical to the product described in Example 37, from 1-(3,4-dichlorophenoxy)-2-(tetrahydropyran-2-yloxy)-3-diphenyl-methylaminopropane, which is not isolated.

EXAMPLE 57

1-(2-Ethoxy-5-trans-propenyl-phenoxy)-2-hydroxy-3-(9-fluorenylamino)-propane, which has a melting point of 119°–121° and is identical to the product described in Example 28, from 1-(2-ethoxy-5-trans-propenyl-phenoxy)-2-tetrahydropyran-2-yloxy)-3-(9-fluorenylamino)-propane, which is not isolated.

EXAMPLE 58 (processes c) and d))

A mixture of 27.6 g of 1-diphenylmethylamino-2-hydroxy-3-chloropropane, 10 ml of a 37% strength solution of formaldehyde and 200 ml of benzene is heated to the reflux temperature, while continuously separating off water. The mixture is then evaporated in vacuo and 3-diphenylmethyl-5-chloromethyloxazolidine is obtained as a yellowish oil which, without purification, is heated together with the reacton solution obtained according to Example 43 from 2.3 g of sodium, 100 ml of ethanol and 17.8 g of 4-trans-propenylguaethol, to 100° in an autoclave for 12 hours. After cooling, the sodium chloride which has precipitated is filtered off. 50 ml of 4 N hydrochloric acid are added to the resulting alcoholic solution of 3-diphenylmethyl-5-(2-ethoxy-5-trans-propenyl-phenoxymethyl)-oxazolidine and the mixture is left to stand for 4 hours at room temperature.

1-(2-Ethoxy-5-trans-propenyl-phenoxy)-2-hydroxy-3-diphenylmethylaminopropane hydrochloride, which has precipitated and is identical to the product described in Example 1, is then filtered off. Melting point: 145°–146°; yield: 15.1g = 33.3% of theory.

The substances which follow are prepared by the same process:

EXAMPLE 59

3-Diphenylmethyl-5-(2-methoxy-4-n-propyl-phenoxymethyl)oxazolidine from 3-diphenylmethyl-5-chloromethyl-oxazolidine and sodium 2-methoxy-4-n-propyl-phenolate; this product is hydrolysed with alcoholic-aqueous hydrochloric acid to give 1-(2-methoxy-4-n-propyl-phenoxy)-2-hydroxy-3-diphenylmethylamino-propane hydrochloride with a melting point of 108°–110°.

EXAMPLE 60

3-Diphenylmethyl-5-(2-methoxy-4-allyl-phenoxymethyl)oxazolidine from 3-diphenylmethyl-5-chloromethyl-oxazolidine and sodium eugenolate*; this produce is hydrolysed with alcoholic-aqueous hydrochloric acid to give 1-(2-methoxy-4-allyl-phenoxy)-2-hydroxy-3-diphenylmethylaminopropane hydrochloride with a melting point of 143°.

*) 2-methoxy-4-alkyl-phenolate

EXAMPLE 61

3-Diphenylmethyl-5-(3,4-dichloro-phenoxymethyl)-oxazolidine from 3-diphenylmethyl-5-chloromethyl-oxazolidine and sodium 3,4-dichlorophenolate; this product is hydrolysed with alcoholic-aqueous hydrochloric acid to give 1-(3,4-dichlorophenoxy)-2-hydroxy-3-diphenylmethylaminopropane hydrochloride with a melting point of 180°–184°.

EXAMPLE 62

If, in Example 58, the 3-(9-fluorenylamino)-2-hydroxy-1-chloropropane prepared according to Example 52 is used in place of 3-diphenylmethylamino-2-hydroxy-1-chloropropane, this gives 3-(9-fluorenylamino)-5-(2-ethoxy-5-trans-propenylphenoxymethyl)-oxazolidine, which is hydrolysed with alcoholic-aqueous hydrochloric acid. 1-(2-Ethoxy-5-trans-propenyl-phenoxy)-2-hydroxy-3-(9-fluorenylamino)-propane hydrochloride is thus formed and is converted into the free base which has a melting point of 119°–121°.

We claim:

1. A compound selected from the group consisting of a 1-(disubstituted phenoxy)-2-hydroxypropylamine derivative of the formula:

wherein
R is lower alkyl, lower alkenyl, lower alkoxy, or chloro;
R' is lower alkyl, lower alkenyl, lower alkoxy, or chloro;
R" is diphenylmethyl or fluoren-9-yl; and
the pharmaceutically acceptable acid addition salts thereof.

2. A compound of the formula:

wherein each of
R and R' independently of the other is selected from the group consisting of alkyl of 1 to 6 carbon atoms; alkenyl of 2 to 7 carbon atoms; alkoxy of 1 to 6 carbon atoms and chloro; and
Q and Q', when taken independently, are each hydrogen or, when taken together, are a carbon-carbon bond, or a pharmaceutically acceptable acid addition acid thereof.

3. A compound according to claim 2 selected from the group consisting of a 1-(disubstituted phenoxy)-2-hydroxypropylamine derivative of the formula:

wherein each of
R and
R' independently of the other is alkenyl of 2 to 7 carbon atoms, alkoxy of 1 to 6 carbon atoms, or chloro; and the pharmaceutically acceptable acid addition salts thereof.

4. A compound according to claim 1 wherein each of R and R', independently of the other, is alkyl of 1 to 3 carbon atoms, alkenyl of 3 carbon atoms, alkoxy of 1 to 3 carbon atoms, or chloro.

5. A compound according to claim 1 wherein each of R and R', independently of the other, is methyl, ethyl, propyl, allyl, propenyl, methoxy, ethoxy, or chloro.

6. A compound according to claim 3 wherein R is 2-methoxy or 2-ethoxy and R' is n-propyl, allyl or propenyl in 4- or 5-position.

7. A compound according to claim 3 wherein each of R and R' are chloro in 2- and 4-, 2- and 5-, or 3- and 4-positions.

8. A compound according to claim 3 which is an acid addition salt with an acid selected from the group consisting of hydrochloric acid, hydrobromic acid, sulfuric acid, phosphoric acid, methanesulfonic acid, acetic acid, lactic acid, succinic acid, maleic acid, fumaric acid, malic acid and tartaric acid.

9. The compound according to claim 3 which is 1-(2-ethoxy-5-propenylphenoxy)-2-hydroxy-3-diphenylmethylaminopropane.

10. The compound according to claim 9 wherein the configuration of the propenyl group is trans.

11. The hydrochloride salt of the compound of claim 10.

12. The compound according to claim 3 which is 1-(2-methoxy-4-allylphenoxy)-2-hydroxy-3-diphenylmethylaminopropane.

13. The hydrochloride salt of the compound of claim 12.

14. The compound according to claim 3 which is 1-(2-ethoxy-5-propenylphenoxy)-2-hydroxy-3-(9-fluorenylamino)propane.

15. The compound according to claim 14 wherein the configuration of the propenyl group is trans.

16. The hydrochloride salt of the compound of claim 15.

17. The compound according to claim 3 which is 1-(3,4-dichlorophenoxy)-2-hydroxy-3-diphenylmethylaminopropane.

18. The hydrochloride salt of the compound of claim 17.

19. The method of combatting cerebrovascular insufficiency and producing psychostimulation in humans and other animals which comprises administering thereto an effective amount of a compound according to claim 1.

20. A pharmaceutical composition comprising an amount of a compound according to claim 1 sufficient to combat cerebrovascular insufficiency and produce psychostimulation in combination with a pharmaceutical carrier.

* * * * *